(12) United States Patent
Whannel et al.

(10) Patent No.: US 11,386,982 B2
(45) Date of Patent: Jul. 12, 2022

(54) PATIENT DATA MANAGEMENT PLATFORM

(71) Applicant: ZOLL Medical Corporation, Chelmsford, MA (US)

(72) Inventors: John R. Whannel, Littleton, CO (US); Gregory D. Mears, Carolina Beach, NC (US)

(73) Assignee: ZOLL Medical Corporation, Chelmsford, MA (US)

( * ) Notice: Subject to any disclaimer, the term of this patent is extended or adjusted under 35 U.S.C. 154(b) by 994 days.

(21) Appl. No.: 14/987,597

(22) Filed: Jan. 4, 2016

(65) Prior Publication Data

US 2016/0196387 A1 Jul. 7, 2016

Related U.S. Application Data

(60) Provisional application No. 62/099,553, filed on Jan. 4, 2015.

(51) Int. Cl.
G16H 10/60 (2018.01)
G16H 15/00 (2018.01)

(52) U.S. Cl.
CPC ............ *G16H 10/60* (2018.01); *G16H 15/00* (2018.01)

(58) Field of Classification Search
None
See application file for complete search history.

(56) References Cited

U.S. PATENT DOCUMENTS 8,050,944 B2 11/2011 Brummel et al.
8,364,501 B2 1/2013 Rana et al.
2002/0004729 A1* 1/2002 Zak .................. G16H 10/60 705/3
2003/0004758 A1* 1/2003 Luttrell .............. G06F 19/328 705/3
2005/0038670 A1 2/2005 Takkar et al.
2005/0038696 A1 2/2005 Kalevik et al.
2006/0053034 A1 3/2006 Hlathein et al.
2006/0071797 A1 4/2006 Rosenfeld et al.
(Continued)

FOREIGN PATENT DOCUMENTS

JP 2005018202 A * 1/2005

OTHER PUBLICATIONS

Gupta, Neeraj Kant. "Modeling and Analysis of Next Generation 9-1-1 Emergency Medical Dispatch Protocols." Order No. 3691048 University of North Texas, 2013. Ann Arbor: ProQuest. Web. Feb. 9, 2022. (Year: 2013).*

(Continued)

*Primary Examiner* — Lena Najarian
(74) *Attorney, Agent, or Firm* — Finch & Maloney PLLC

(57) ABSTRACT

A patient data management platform, e.g., a community paramedicine platform, which may also be referred to as a mobile integrative health platform or system, may include a web-based, cloud-based, and/or software-based system for tracking patients and patient visits by health care providers, paramedics or other emergency medical services ("EMS") professionals in an out of hospital, mobile, and/or non-emergency context. Such a platform performs functions and data input, visit logging, and reporting tasks that are distinct from that of a traditional EMS electronic patient care reporting system.

25 Claims, 33 Drawing Sheets

(56) References Cited

U.S. PATENT DOCUMENTS

| | | | |
|---|---|---|---|
| 2008/0103823 A1* | 5/2008 | Papa | G06Q 10/0637 705/2 |
| 2009/0044987 A1* | 2/2009 | Taylor | G01G 23/3728 177/245 |
| 2009/0125326 A1* | 5/2009 | Wasson | G06F 19/3418 705/2 |
| 2011/0009760 A1 | 1/2011 | Zhang et al. | |
| 2011/0021140 A1* | 1/2011 | Binier | H04B 5/0043 455/41.1 |
| 2011/0124987 A1 | 5/2011 | Papazoglou et al. | |
| 2011/0295078 A1 | 12/2011 | Reid et al. | |
| 2012/0109051 A1* | 5/2012 | Harrell | A61F 5/0006 604/77 |
| 2012/0191476 A1 | 7/2012 | Reid et al. | |
| 2013/0085106 A1* | 4/2013 | Pedersen | A61K 31/41 514/11.6 |
| 2013/0191161 A1* | 7/2013 | Churchwell | G06Q 50/24 705/3 |
| 2013/0261409 A1* | 10/2013 | Pathak | A61B 5/0022 600/301 |
| 2013/0297344 A1 | 11/2013 | Cosentino et al. | |
| 2014/0114687 A1 | 4/2014 | Frank et al. | |
| 2014/0279807 A1* | 9/2014 | Dimitrijevic | G06N 5/025 706/47 |
| 2014/0365234 A1 | 12/2014 | Saunders | |
| 2014/0365241 A1 | 12/2014 | Dillie et al. | |
| 2015/0186610 A1* | 7/2015 | Sansale | G16Z 99/00 715/736 |
| 2015/0248532 A1* | 9/2015 | Rajasenan | G06Q 50/22 705/2 |
| 2015/0363563 A1* | 12/2015 | Hallwachs | H04B 5/0062 705/3 |

OTHER PUBLICATIONS

International Search Report and Written Opinion issued by the U.S. Patent and Trademark Office as International Searching Authority in International Application PCT/US2016/012087, dated Jun. 9, 2016 (18 pages).

Beck, et al., "Mobile Integrated Healthcare Practice: A Healthcare Delivery Strategy to Improve Access, Outcomes, and Value", Manuscript Concensus Meeting, Chicago, IL, Dec. 9-10, 2012, 8 pages.

Epic Software, website, www.epic.com/software-index.pho, accessed Jan. 27, 2016, 1 page.

ESO Healthcare Connected Software Suite; www.esosolutions.com/our-products/epcr-suite/, accessed Jan. 27, 2016, 4 pages.

HealthCall, "Empowering Community Paramedicine", http://www.healthcall.com/solutions-products/community-paramedicine/, 2014, accessed Jan. 27, 2016, 4 pages.

HealthCall, software website, http://www.healthcall.com/, 2014, accessed Jan. 27, 2016, 4 pages.

ImageTrend, Inc., Health Information Hub, Truly Connected Health Information brochure, 2014, 2 pages.

* cited by examiner

Patient history

Medical History

| (Idiopathic) normal pressure hydrocephalus | | 3-methylglutaconic aciduria |
| (Induced) termination of pregnancy w oth and unsp comp | Add > | Abdominal and pelvic pain |
| (Induced) termination of pregnancy with other complications | < Delete | |
| (Induced) termination of pregnancy with unsp complications | | |
| 46, XX true hermaphrodite | | |
| Abdominal actinomycosis | | |
| Abdominal aortic aneurvsm, ruptured | | |

Load more...

Medication Allergies

(PHTHALOCYANINATO(2-)) COPPER
[13C] urea
1-(4-(4-CHLOROPHENYL)-3-PHENYL-2-BUTENYL)-PYRROLIDINE 1,5-NAPHTHALENEDISULFONATE
1,10-decanediol
1,1-difluoroethane
1,2,6-hexanetriol
1,2-DIARACHIDOYL-SN-GLYCERO-3-PHOSPHOCHOLINE Add >
< Delete 1,2-DIOLEOYL-SN-GLYCERO-3-PHOSPHOCHOLINE Load more...

Food/Environmental Allergies

Alcohol products
Almond oil
Aluminium
Ant sting
Aspartame
Bee venom
Boric acid
Caffeine
Carrot Add >
< Delete Animal dander Load more...

Social History

History (social) notes here.

Save  Cancel

Community Paramedicine - v4.1.0.11

Community Paramedicine   Add a patient   View patient list for all products

Ben Franklin
Congestive Heart Failure, Male, 94 years

Congestive Heart Failure - Admitted
- Log a visit
- Medication
- History
- Attachments
- Audits Reporting

Patient Audits page

Patients

| ActionTimeStamp | | ActionTypeKey | User | Details |
|---|---|---|---|---|
| | | No results found. | | |

Showing 0 to 0 of 0 entries
Show [50 ▼] entries

Previous  Next

Community Paramedicine - v4.1.0.11

FIG. 10

Community Paramedicine    Add a patient    View patient list for all products    Reporting

Ben Franklin
Congestive Heart Failure, Male, 94 years

414 →

| Congestive Heart Failure - Admitted ② |
|---|
| 12/28/2014 12:30 |
| 12/27/2014 16:07 |
| ⦿ Log a visit |
| Medication |
| History |
| Attachments |
| Audits |

Log a visit > Medications > Vitals > Labs > Interventions > Narrative

Log a visit

Scheduled date/time of visit:*
[ 12/28/2014 15:39 ▽ ]

Type of visit:*
[ Follow-up ▽ ]

Medical specialist 1:*
[ Joe Jones ▽ ]

Medical specialist 2:
[ Jack Smith ▽ ]

Vehicle:*
[ CP-1 ▽ ]

Run Number:
[ 2 ]

En route:
[ 12/28/2014 15:31 ]

On scene:
[ 12/28/2014 15:39 ]

Time available:
[ 12/28/2014 15:41 ]

[ Save ] [ Cancel ]

[ Next ] ← 415

Community Paramedicine - v4.1.0.11

Vitals

Recorded on:*
12/28/2014 15:44

Popup Keypad

BP systolic
190

BP diastolic
75 | mmHg

Heart rate:
75 | beats per minute

Weight
190 | lbs

Respiratory rate:
13 | breaths per minute

Temperature:
98.6 | °F

SpO2:
99 | %

Air condition during SpO2 test:
◉ Room air  ○ Supplemental oxygen:

Supplemental oxygen:
Select an item ▼ | lpm

Left lung sounds:
Normal ▼

Right lung sounds:
Normal ▼

Lung sound notes:
[lung sound notes inserted]

Save | Cancel

Next

Community Paramedicine - v4.1.0.11

Community Paramedicine     Add a patient     View patient list for all products

Ben Franklin
Congestive Heart Failure, Male, 94 years

Reporting

| Congestive Heart Failure - Admitted ③ |
|---|
| 12/28/2014 15:39 |
| 12/28/2014 12:30 |
| 12/27/2014 18:07 |
| ⊕ Log a visit |
| Medication |
| History |
| Attachments |
| Audits |

Log a visit › Medications › Vitals › Labs › Interventions › Narrative

Patient narrative

Program type: Congestive Heart Failure

Subjective ⌃

Describe the patient and their medical condition:

How has the patient's condition changed since the last visit?

Objective ⌃

Significant exam findings:

Additional findings such as labs or 12-lead ECG:

Ben Franklin, Male, 94 years, Program status: Admitted | Program type: Congestive Heart Failure

Program goals:
Keep out of hospital for 30 days

Providers:
x - indicates patient's medical home

Purpose of report:
Status report for primary care Physician.

Interventions Summary:

| Date | Procedure | ECG | Medication | IV |
|---|---|---|---|---|
| 12/27/2014 | 12 lead ECG | | Adenosine 1 Grams | 1 started, 1 stopped |
| 12/28/2014 | 3 lead electrocardiographic monitoring | | | |

Medications Summary:
Epinephrine 0.2 gms, After meals (p.c.)

FIG. 24

Add a patient
*Areas marked with a * are required.*

Patient details

First name*  Middle name  Last name*

Date of birth*  Date of death  Age  Sex*
[Select item]

Social security number  Patient ID  Marital status
[0]  [Select item]

Address  Suite/Apartment

Country  State/Province  City
[United States]  [Select item]

Email address  Postal code
Enter postal code with no spaces

Preferred contact method
[Select item]
Select the preferred contact method

Contact number
[Select item ▼]
Add contact number ⊗

Emergency contact

First name  Last name  Relationship
[Select item]

Address  Suite/Apartment

Country  State/Province  City
[United States]  [Select item]

Postal code
Enter postal code with no spaces

Contact number
[Select item ▼]
Add contact number ⊗

FIG. 25

Billing details

Employment status
[Select item]

Student status
[Select item]

Address
[ ]

Suite/Apartment
[ ]

City
[ ]

County
[ ]

Country
[United States]

State/Province
[Select item]

Postal Code
[ ]

Enter postal code with no spaces

Patient insurance

[New insurance]

no insurance

Providers

Name
[Select a Provider]

Phone
[ ]

Medical home
[ ]

[Add a Provider ⊕]

[Save] [Save & Close] [Cancel]

Patients

Add patients to your agency

⊕ Add a patient

| Patient name | Date of birth | Social security number | Enabled | |
|---|---|---|---|---|
| Alpha, Alf | 1951-12-28 | | ⊘ | ⊗ |
| Doe, Jane | 1930-05-31 | | ⊘ | ⊗ |
| Doe, John | 1951-07-11 | | ⊘ | ⊗ |
| Franklin, Ben | 1920-02-11 | | ⊘ | ⊗ |
| Johnson, Janice | 1927-02-16 | | ⊘ | ⊗ |
| Jones, Sally | 1941-10-20 | | ⊘ | ⊗ |
| Mid, Loe | 1968-10-02 | ???-??-5666 | ⊘ | ⊗ |
| Smith, Jane | 1965-10-02 | ???-??-4444 | ⊘ | ⊗ |
| Test, Arnold | 1957-11-05 | ???-??-6785 | ⊘ | ⊗ |

PATIENT DATA MANAGEMENT PLATFORM

RELATED APPLICATIONS

This application relates to and claims priority under 35 U.S.C. § 119(e) to U.S. Provisional Patent Application No. 62/099,553, entitled "PATIENT DATA MANAGEMENT PLATFORM," which was filed on Jan. 4, 2015, the contents of which, are incorporated by reference herein in their entirety.

TECHNICAL FIELD

Embodiments of the present disclosure relate generally to platforms that facilitate coordination of patient visits and goal tracking for a mobile integrated health system.

BACKGROUND

Traditional emergency medical service ("EMS") patient encounters are tracked to capture and aggregate information related to an emergency medical response, for example as described in U.S. Patent Application Publication No. 2011/0295078, published on Dec. 1, 2011, which is incorporated by reference herein in its entirety for all purposes. However, paramedics and EMS crews often perform other tasks, such as non-emergency transports from facility to facility. Sometimes paramedics and EMS crews are asked to make scheduled non-emergency medical visits to patients for various reasons. Because such visits can be non-emergency in nature, the documentation of such visits often does not fit well into the documentation framework for a traditional EMS visit, and/or such visits are often documented and/or reported informally or inconsistently.

SUMMARY

In Example 1, a patient data management system according to embodiments of the present disclosure includes: a medical database configured to store for each patient therein a patient record comprising at least one program goal specific to the patient, the at least one program goal comprises meeting a condition during or within a time period or within a predetermined number of visits; and a server configured to be in communication with at least one mobile computing device, the server comprising a processor and a memory, the memory including instructions that when executed by the processor cause the processor to: prompt a user to enter information about the patient associated with the at least one program goal and obtained during a first visit of the patient; prompt the user to enter information about the patient associated with the at least one program goal and obtained during a second visit of the patient; and using the information about the patient from the first visit and the second visit, display an indication of progress of the patient in meeting the at least one program goal.

Example 2 is the patient data management system of Example 1, wherein the indication of progress is a program status associated with the at least one program goal.

Example 3 is the patient data management system of any of Examples 1 to 2, wherein the indication of progress comprises a compilation of one or both of quantitative and qualitative information entered about the patient during the first and second medical visits.

Example 4 is the patient data management system of any of Examples 1 to 3, the memory further including instructions that when executed by the processor further cause the processor to: compare the information from the second medical visit to the information from the first medical visit to assist in evaluation and/or treatment during the second medical visit.

Example 5 is the patient data management system of any of Examples 1 to 4, wherein assisting in evaluation and/or treatment during the second medical visit comprises alerting the health care provider to an inconsistency in the information between the first medical visit and the second medical visit.

Example 6 is the patient data management system of any of Examples 1 to 5, wherein the at least one program goal comprises meeting a condition during or within a time period of at least thirty days.

Example 7 is the patient data management system of any of Examples 1 to 6, wherein the patient is a congestive heart failure patient, and wherein the at least one program goal is avoiding readmission of the patient to a hospital for the time period.

Example 8 is the patient data management system of any of Examples 1 to 7, wherein the information for the first and second medical visits includes a patient weight, and wherein the indication of progress indicates whether a change in the patient weight was within an acceptable range during the time period.

Example 9 is the patient data management system of any of Examples 1 to 8, wherein the patient is a diabetic patient, and wherein the at least one program goal is healing a wound during the time period.

Example 10 is the patient data management system of any of Examples 1 to 9, wherein the information for the first and second medical visits includes a size and infection status of the wound, and wherein the indication of progress indicates whether healing of the wound occurred during the time period.

Example 11 is the patient data management system of any of Examples 1 to 10, wherein the patient is a substance abuse patient, and wherein the at least one program goal is referring the patient to a mental health center for substance abuse treatment without using emergency medical services.

Example 12 is the patient data management system of any of Examples 1 to 11, wherein the information for the first and second medical visits includes vital signs and physiological examination information to confirm whether the patient can be referred to the mental health center without requiring emergency medical services.

Example 13 is the patient data management system of any of Examples 1 to 12, wherein the predetermined number of visits is one, and the information for the first and second medical visits includes notation of non-emergency needs of the patient to refer the patient to other community resources.

Example 14 is the patient data management system of any of Examples 1 to 13, wherein the at least one program goal is selected from a set of two or more program goals that the patient data management system is configured to track, the set of two or more program goals comprising two or more of: (a) avoiding readmission of a patient to a hospital for a particular time period; (b) healing a wound of a patient during a particular treatment period; (c) referring a patient to a mental health center for substance abuse treatment without using emergency medical services; and (d) reducing a patient's use of emergency medical services over a particular time period.

Example 15 is the patient data management system of any of Examples 1 to 14, wherein the at least one program goal is selected from a set of three or more program goals that the patient data management system is configured to track, the set of three or more program goals comprising three or more of: (a) avoiding readmission of a congestive heart failure patient to a hospital for a particular time period; (b) healing a wound of a diabetic patient during a particular treatment period; (c) referring a substance abuse patient to a mental health center for substance abuse treatment without using emergency medical services; and (d) reducing a high-frequency emergency medical services (EMS) patient's use of EMS over a particular time period.

Example 16 is the patient data management system of any of Examples 1 to 15, wherein the user is a health care provider, wherein the first and second visits are first and second medical visits of the health care provider to the patient, wherein the at least one mobile computing device is configured to be carried with the health care provider during a medical visit by the health care provider to the patient, and wherein the memory further includes instructions that when executed by the processor further cause the processor to prompt the health care provider to enter the information about the patient obtained during the first visit of the patient during the first visit, and to prompt the health care provider to enter the information about the patient obtained during the second visit of the patient during the second visit.

In Example 17, a patient data management system according to embodiments of the present disclosure includes: a medical database configured to store for each patient therein a patient record comprising at least one of a program type, a program status, and a program goal specific to the patient; and a server configured to be in communication with at least one mobile computing device configured, the server comprising a processor and a memory, the memory including instructions that when executed by the processor cause the processor to: receive a scheduling request for a medical visit to a patient; search the medical database for the patient record for the patient; wherein, if the patient record for the patient is identified, update the at least one of the program type, the program status, and the program goal for the patient based on the scheduling request; or wherein, if the patient record for the patient is not identified, create the at least one of the program type, the program status, and the program goal for the patient based on the scheduling request; and receive a request from the at least one mobile computing device sent to the server to log the medical visit to the patient in the medical database.

Example 18 is the patient data management system of any of Examples 1 to 17, the memory further including instructions that, when executed by the processor, cause the processor to display on the at least one mobile computing device information entered during the scheduling request and the medical visit, the information indicative of progress of the patient toward the program goal.

Example 19 is the patient data management system of any of Examples 1 to 18, wherein the information comprises a compilation of information entered during the scheduling request and the medical visit.

Example 20 is the patient data management system of any of Examples 1 to 19, wherein the program type is associated with congestive heart failure, wherein the program goal is to prevent readmission of the patient to a hospital for a period of time.

Example 21 is the patient data management system of any of Examples 1 to 20, wherein the information includes information about a weight of the patient, the information indicating whether the patient's weight exceeds a certain weight or falls outside of a certain weight range indicative of fluid buildup.

Example 22 is the patient data management system of any of Examples 1 to 21, wherein the program type is associated with a patient wound and wherein the program goal is to improve wound healing within a predetermined time period.

Example 23 is the patient data management system of any of Examples 1 to 22, wherein the information includes information about one or more of a size and an infection status of the patient wound, the information indicating whether healing of the patient wound has improved since the scheduling request or the medical visit.

Example 24 is the patient data management system of any of Examples 1 to 23, wherein the program type is associated with a mental health condition and wherein the program goal is to place the patient into a mental health system.

Example 25 is the patient data management system of any of Examples 1 to 24, wherein the information includes information about a baseline condition of the patient, the baseline condition including at least vital sign and psychological assessment information, the information indicating whether the patient, during the medical visit, is at or near the baseline condition or requires emergency medical attention.

Example 26 is the patient data management system of any of Examples 1 to 25, wherein the program type is associated with overly frequent requests for emergency room services and wherein the program goal is to reduce a frequency of the overly frequent requests for emergency room services of the patient.

Example 27 is the patient data management system of any of Examples 1 to 26, wherein the information includes information about a frequency of requests of the patient for emergency medical services over a particular time period.

In Example 28, a patient data management system according to embodiments of the present disclosure includes a medical database configured to store for each patient therein a patient record comprising at least one program goal specific to each patient; and a server configured to be in communication with mobile computing devices configured to be carried with a health care providers during visits by the health care providers to the patients, the server comprising a processor and a memory, the memory including instructions that when executed by the processor cause the processor to: during each medical visit by the health care providers to the patients, prompt the health care provider to enter evaluation and/or treatment information of the patient associated with the at least one program goal for the patient; wherein the at least one program goal is selected so as to further at least one community goal, and wherein the at least one community goal includes one or more of: reducing hospital readmission rate for the set of the patients, and reducing frequency or extent of use of emergency medical services for the set of the patients.

Example 29 is the patient data management system of any of Examples 1 to 28, wherein the at least one program goal specific to each patient is selected from among two or more of the following program goals which the server is further configured to track: (a) avoiding readmission of a patient to a hospital for a particular time period; (b) healing a wound of a patient during a particular treatment period; (c) referring a patient to a mental health center for substance abuse treatment without using emergency medical services; and (d) reducing a patient's use of emergency medical services over a particular time period.

Example 30 is the patient data management system of any of Examples 1 to 29, the at least one program goal specific to each patient selected from among three or more of the following program goals which the server is further configured to track: (a) avoiding readmission of a patient to a hospital for a particular time period; (b) healing a wound of a patient during a particular treatment period; (c) referring a patient to a mental health center for substance abuse treatment without using emergency medical services; and (d) reducing a patient's use of emergency medical services over a particular time period.

In Example 31, a patient data management system according to embodiments of the present disclosure includes a medical database configured to store for each patient therein: a patient record comprising at least one of a program type, a program status, and a program goal specific to the patient; and a list of medications specific to the patient; and a server configured to be in communication with a mobile computing device configured to be carried with a health care provider during a medical visit by the health care provider to a patient, at least one of before, during, and after the medical visit, the server comprising a processor and a memory, the memory including instructions that when executed by the processor cause the processor to: receive a request from the mobile computing device sent to the server to log a medical visit to a first patient in the medical database; update at least one of a program type, a program status, a program goal specific to the first patient, and a list of medications specific to the first patient based on information entered into the mobile computing device during the medical visit to the first patient; and generate an alert based on at least the entered information into the mobile computing device.

Example 32 is the patient data management system of any of Examples 1 to 31, wherein the entered information comprises at least one of a physiological measurement, a vital sign, a health goal, a suggested care plan, and medication information.

Example 33 is the patient data management system of any of Examples 1 to 32, wherein the alert is generated when the physiological measurement is outside a first range.

Example 34 is the patient data management system of any of Examples 1 to 33, wherein the alert is generated when the vital sign is outside a second range.

Example 35 is the patient data management system of any of Examples 1 to 34, wherein the alert is generated when the health goal is not reached by the patient.

Example 36 is the patient data management system of any of Examples 1 to 35, wherein the alert is generated when the suggested care plan is not followed by the patient.

Example 37 is the patient data management system of any of Examples 1 to 36, wherein the alert is generated when at least one of the dosage of the medication and the type of the medication requires updating.

In Example 38, a patient data management system according to embodiments of the present disclosure includes: a medical database configured to store for each patient therein: a patient record comprising at least one of a program type, a program status, and a program goal specific to the patient; and a list of medications specific to the patient; and a server configured to be in communication with a mobile computing device configured to be carried with a health care provider during a medical visit by the health care provider to a patient, at least one of before, during, and after the medical visit, the server comprising a processor and a memory, the memory including instructions that when executed by the processor cause the processor to: receive a request from the mobile computing device sent to the server to log a medical visit to a first patient in the medical database; query the medical database to retrieve a list of medications specific to a first patient; send the retrieved list of medications from the server to the mobile computing device; cause the mobile computing device to display the list of medications in a user interface screen to permit the health care provider to reconcile a list of medications for the medical visit with the list of medications from the medical database; receive the list of medications for the medical visit sent from the mobile computing device; and update the list of medications specific to the first patient in the medical database.

Example 39 is the patient data management system of any of Examples 1 to 38, further comprising proposing to the patient at least one of a new medication, discontinuing a first existing medication specific to the first patient, and adjusting the dosage of a second existing medication specific to the first patient.

Example 40 is the patient data management system of any of Examples 1 to 39, further comprising generating an alert based on the updated list of medications.

In Example 41, a patient data management system according to embodiments of the present disclosure includes: a server configured to be communicably coupled with: a facility computing device configured for use at a health care facility; and a mobile computing device configured to be carried with a health care provider during a medical visit by the health care provider to the patient, and the server comprising a processor and a memory, the memory including instructions that when executed by the processor cause the processor to: receive from the facility computing device a care plan for the patient associated with a discharge of the patient from the health care facility; display some or all of the care plan on the mobile computing device during the medical visit, wherein the medical visit occurs after the discharge; prompt the health care provider to enter information associated with the patient's compliance with the care plan; and receive from the mobile computing device the information associated with the patient's compliance with the care plan.

Example 42 is the patient data management system of any of Examples 1 to 41, wherein the instructions further cause the processor to display on the mobile computing device during the medical visit suggestions for helping the patient comply with the care plan.

Example 43 is a patient data management method, wherein the steps of the method comprise the instructions executed by the processor of the patient data management system of any of Examples 1 to 42, regardless of which hardware or instrumentality performs such steps.

In Example 44, a patient data management or documentation platform or system according to an embodiment of the present disclosure includes one or more of a mobile computing device, the mobile computing device configured to be carried with a health care provider, e.g., a paramedic, during a medical visit, e.g., a non-emergency medical visit, by the health care provider to a patient; a server, the server and mobile computing device configured to be in communication during or after the medical visit; a medical database having stored for each patient therein: an indication of at least one of a program type, a program status, and a program goal specific to the patient; a list of medications specific to the patient; a processor and a database, the database including instructions that when executed by the processor cause the processor to: receive a request from the mobile computing device sent to the server to log a medical visit, e.g., a new non-emergency medical visit, to the patient in the medical database, querying the medical database to retrieve the list of medications and sending the list of medications from the server to the mobile computing device, causing the mobile computing device to display the list of medications in a user interface screen to permit the health care provider to reconcile a list of medications for the medical visit with the list of medications from the medical database; receiving the list of medications for the medical visit sent from the mobile computing device to the server; and storing the list of medications for the medical visit in the medical database.

In Example 45, a community paramedicine system according to an embodiment of the present disclosure includes a mobile computing device, the mobile computing device configured to be carried with a health care provider, e.g., a paramedic, during a medical visit, e.g., a non-emergency medical visit, by the health care provider to a patient; a server, the server and mobile computing device configured to be in communication during the medical visit; a medical database having stored for each patient therein: an indication of at least one of a program type, a program status, and a program goal specific to the patient; a processor and a database, the database including instructions that when executed by the processor cause the processor to: receive a request from the mobile computing device sent to the server to log a medical visit to the patient in the medical database, causing the mobile computing device to prompt for entry of narrative text relating to an assessment and a plan for the medical visit, receiving the narrative text sent from the mobile computing device to the server, and storing the narrative text in the medical database.

In Example 46, a patient data management system according to an embodiment of the present disclosure includes a web-based electronic platform and user interface with which patients can be added to the patient data management system, and with which medical visits, e.g., non-emergency, mobile, community paramedicine, and/or out of hospital visits, by health care providers, e.g., paramedics or other health care practitioners, to the patients can be logged, reviewed, and/or reported including one or more of the date and time of the visit, any medications, vital signs, lab analysis results, interventions, and/or patient assessment and/or plan narratives associated with the visit. In such a system, at least some data regarding the medications, vital signs, lab analysis results, interventions, and/or patient assessment and/or plan narratives is obtained by the patient data management system automatically from one or more devices in communication with the patient or the patient's fluid or tissue during the medical visit, according to an embodiment of the present disclosure.

While multiple embodiments are disclosed, still other embodiments of the present disclosure will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

Various objects, features, and advantages of the disclosed subject matter can be more fully appreciated with reference to the following detailed description of the disclosed subject matter when considered in connection with the following drawings.

FIGS. 4-31 illustrate screen shots from a user interface of an exemplary patient data management platform, e.g., a community paramedicine platform or EMS mobile health platform, according to embodiments of the present disclosure.

Figure 1:
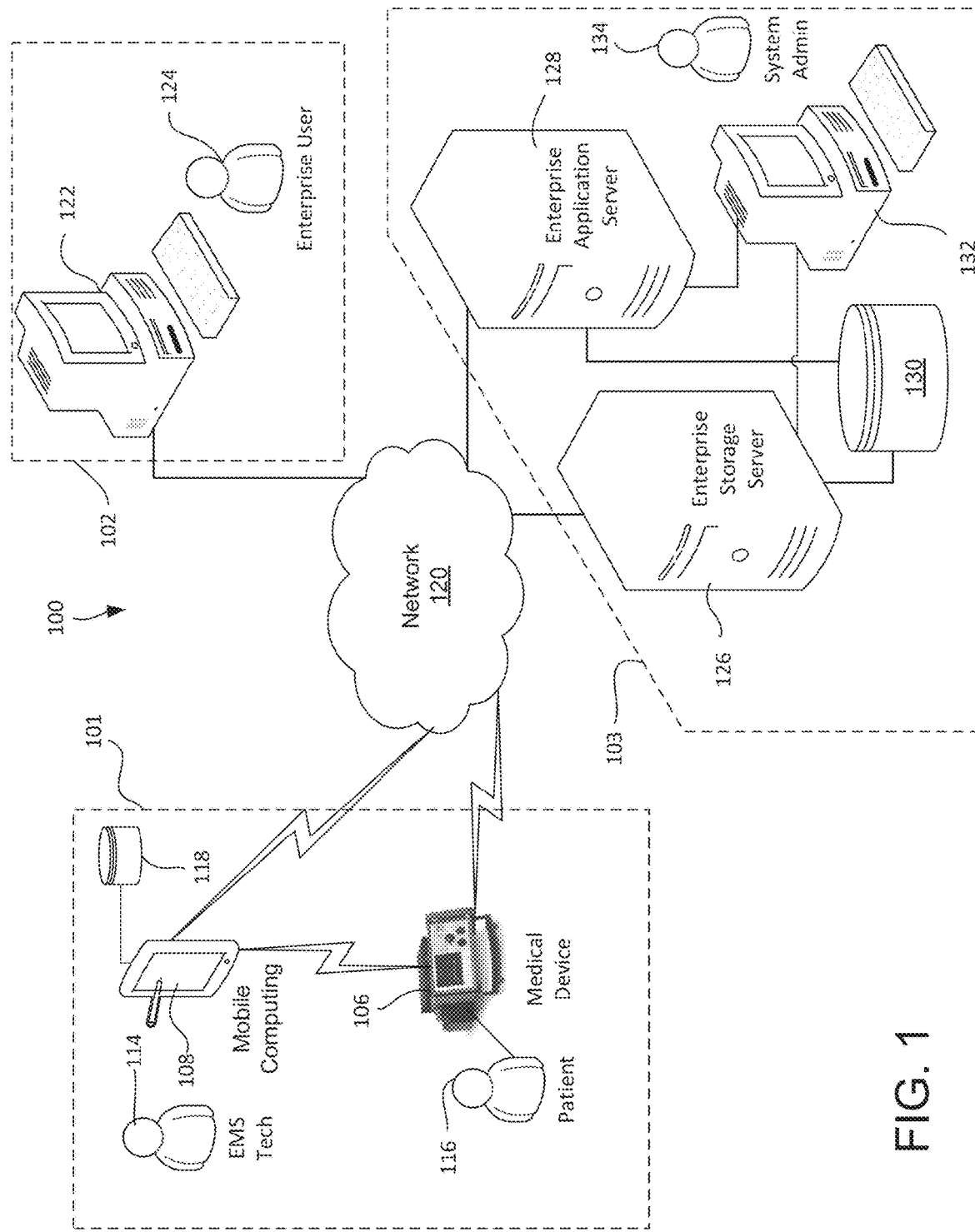
FIG. 1 illustrates a patient data management system, according to embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the present disclosure

DETAILED DESCRIPTION

In the following description, numerous specific details are set forth regarding the systems and methods of the disclosed subject matter and the environment in which such systems and methods may operate, in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that the embodiments described below are only examples, and that it is contemplated that there are other systems and methods that are within the scope of the disclosed subject matter.

A patient data management platform or system provides a web-based, or cloud-based, system for tracking patients and patient visits by health care providers, e.g., paramedics, other emergency medical services ("EMS") professionals, hospice care providers, or any health care professional or practitioner who administers health care in a non-emergency, out-of-hospital, mobile, and/or community paramedicine context, environment or setting, according to certain embodiments of the present disclosure. In certain embodiments, such a patient data management platform or system may alternatively be referred to as a community paramedicine platform or system, mobile integrated health platform or system, an EMS mobile health platform or system, a mobile integrative health system, an EMS community health system, an EMS public health system, and/or an EMS injury prevention system, and such terms may be used interchangeably throughout this application. Additionally, such platforms or systems may be used in conducting one or more programs, including without limitation: patient data management programs, community paramedicine programs, mobile integrated health programs, an EMS mobile health program, a mobile integrative health program, an EMS community health program, an EMS public health program, and/or an EMS injury prevention program, and such terms may be used interchangeably throughout this application. A patient data management platform or system may be, without limitation, web-based, cloud-based, and/or operatingsystem based (e.g., Windows-based, iOS-based, and/or Android-based), according to embodiments of the present disclosure.

As described above, traditional EMS patient encounters are tracked to capture and aggregate information related to an emergency medical response. Because medical visits, e.g., non-emergency medical visits, can be non-emergency in nature, the documentation of such visits often does not fit well into the documentation framework for a traditional EMS visit, and/or such visits may be documented and/or reported informally or inconsistently.

Furthermore, the goal of a typical EMS encounter is to immediately stabilize the patient and, if necessary, transport the patient to a facility for in-depth diagnosis and care. However, the goals of a non-emergency, community paramedicine program are often different, diverse, and longer-term and thus it can be difficult to document and report such visits in an effective manner using existing EMS charting or data aggregation systems, even though such community paramedicine visits may be performed by the same professionals, with the same vehicles, and with the same equipment used in a typical EMS response. In some embodiments, a patient data management platform, community paramedicine platform is patient-based rather than incident-based. Existing traditional EMS charting systems are incident-based.

A patient data management platform, e.g., a community paramedicine platform, according to certain embodiments of the present disclosure can include one or more of the following non-limiting features and/or characteristics: it is longitudinal patient-centered care provided by emergency medical services; it is focused on a specific condition or community health issue; it is scheduled as opposed to emergent in nature (e.g., it is non-emergent); the patient may be transported to an emergency department or alternative healthcare provider as the patient's condition necessitates; and/or it documents the service (operations) provided in addition to the care provided. One or more of these features and/or characteristics can distinguish a patient data management platform 100 according to embodiments of the present disclosure from a traditional home health electronic health record platform, a traditional physician clinic electronic health record platform, and a traditional hospital electronic health record platform.

According to certain embodiments of the present disclosure, a patient data management platform, e.g., a community paramedicine platform, may document the service and/or operations and/or care and/or related performance of an agency and/or EMS crew and/or healthcare provider and/or healthcare facility.

The goals for a patient data management platform, e.g., a community paramedicine platform, may vary. For example, one goal can be to stop system abuse. For example, some patients routinely call "911" or emergency dispatch systems for non-emergency situations, or directly contact advanced or specialist providers without proper referral or before being diagnosed by a primary care physician or referred by a paramedic. Another goal of a patient data management system can be to keep a patient out of the hospital for at least thirty days (or some other period of time) following discharge from the hospital, which can be an important tracking metric for performance of hospitals and care providers. Yet another goal of a patient data management platform can be to evaluate a patient and triage the patient for a potential emergency room visit, in other words to determine if an emergency room visit would be appropriate or to perform some of the pre-admission or admission activities at the patient's location instead of at the emergency room. Yet another goal of a patient data management platform can be to enable scheduling of medical visits that can automatically create documentation for the medical visits. Yet another goal of a patient data management platform can be to generate alerts based on information collected before, during, or after a medical visit. Yet another goal of a patient data management platform can be to perform tasks related to medication inventory, such as medication audit, addition of new medication, or discontinuing of an existing medication. Yet another goal of a patient data management platform can be to collect information and determine compliance of a particular patient with a care plan. Patient data management platforms may have or accomplish other goals related to patient care, evaluation, and reporting, including customized goals specific to particular patient populations, geographies, and care provider networks. Yet other goals of a patient data management platform may include injury prevention and/or immunization. A patient data management platform as described herein may include all or a subset of such goals, for example. Also, the goal or goals may be documented with respect to each particular patient, e.g., for a community paramedicine platform, as described below, and the goals may be different for different patients of the same community paramedicine platform or system.

Certain embodiments of the present disclosure include a technological web-based platform for community paramedicine, other out of hospital, non-emergency and/or mobile health care services. A non-emergency medical visit may be, for example, a visit by EMS personnel that did not result from a "911 call" or other emergency dispatch call or contact. The rules for who can refer a patient to the patient data management platform, e.g., a community paramedicine platform, can be set by a company, a local municipality, or other local, state, or federal governmental or regulatory agency. For example, an EMS company or municipality responsible for an EMS system may permit entry of a new patient into the community paramedicine platform based on referrals by paramedics, physicians, hospitals, emergency communications (e.g., "911" call center) operators, and/or others. The same patient data management platform or community paramedicine platform can be used to track patients and related goals, program types, and program status across different EMS companies and healthcare facilities and providers.

When a new patient is added to the patient data management platform, e.g., a community paramedicine platform, a "program type" may be associated with the patient. Such program types may be of any design or purpose, but can help the users of the patient data management platform understand why the patient is part of the platform, how specific actions can be taken to document or report on the visits to the patient and how the goals set for the patient can be specifically accomplished. Such program types may also be related to specific treatment pathways or protocols related to patient visits, as well as criteria for documenting or implementing changes in the patient's status or treatment. Program types may include, for example, "evaluate and refer," "chronic obstructive pulmonary disease," "congestive heart failure," "hotspotter" or "loyal customer" (e.g., a "high-cost patient" for which a community paramedicine program may be designed to maintain a level of care at a lower cost), a substance abuse and/or mental health referral program, and "myocardial infarction." A patient data management platform may alternatively include a subset or variation(s) of these program types, or additional program types or variations, for example.

The patient data management platform can also include a "program status" for each patient, for example "re-hospitalized," "unable to contact," "admitted," "ineligible," "placed," "removed," "refused," "deferred," "task complete," "referred," and "discharged." A patient data management platform may alternatively include a subset or variation(s) of these program statuses, or additional program statuses or variations, for example. Such program status assists users of the platform in understanding where a particular patient is at with respect to their program type, their goal(s), and/or the healthcare system in general. For example, paramedic visits that would normally be associated with a "congestive heart failure" patient may be delayed or rescheduled if the patient has been or is currently "re-hospitalized," or if during a non-emergency visit the paramedic determines that the patient should be re-hospitalized, the paramedic can transport the patient to the hospital and change the patient's status to "re-hospitalized."

Using goals, program types, and program status for patients in, e.g., a community paramedicine system, permits tracking, accountability, billing, performance metrics, and improved patient care, according to some embodiments. A given patient may also be part of more than one "program type" within community paramedicine or other platforms, and the same patient visit can be used to document the information or conduct the visit treatment protocol associated with each of the "program types," according to certain embodiments.

The patient data management platform can also provide the ability to schedule an appointment for a visit with a patient and utilize the appointment information to generate visit documentation related to the particular patient and/or the particular visit. For example, the platform can access a patient record to update the program type, the program status, and/or the program goal for an existing patient, based on the scheduled appointment. Alternatively, the platform can create a new patient record to populate a new program type, a new program status, and/or a new program goal for a new patient, based on the scheduled appointment. The platform can therefore merge a scheduling capability with documentation for the patient, for example, based on the patient medical history, the type of visit, and a particular care plan.

According to alternative embodiments, the patient data management platform can generate alerts. The alerts can be customized based on a particular patient, such as alerts based on a patient's physiological measurements, vital signs, health goals, suggested care plan, and medication. For example, the patient data management platform can generate an alert if a patient's physiological measurement, e.g., glycose level, is outside an appropriate range for the particular patient. As an additional example, the patient data management platform can generate an alert if a patient's vital signs, e.g., blood pressure, is outside an appropriate range for the particular patient. As an additional example, the patient data management platform can generate an alert if a goal set for a particular patient is not met, e.g., when a patient has not reached a target weight. As an additional example, the patient data management platform can generate an alert if a patient does not follow a care plan set by his physician. As an additional example, the patient data management platform can generate an alert if, for example, a medication dosage is not appropriate for a patient's vital signs or if a patient is taking duplicate medication, such as when a patient is taking a brand name drug and the generic drug with the same active ingredient.

According to alternative embodiments, the patient data management platform can perform medication inventory functions. For example, a paramedic visiting a patient can audit the patient's medication with the patient. During the audit, the paramedic can enter new medication, for example, through an interface on a mobile device, which can include a drop down menu or an autofill prompt. The patient data management platform can also provide a list of medications on the patient's record. The patient data management platform can propose discontinuing a particular medication, activating a new medication, or adjusting the dosage for a particular medication, based for example, on information collected before or during the visit. As discussed above, the patient data management platform can generate alerts based on medications specific to a particular patient. For example, the platform can generate medication-related alerts, when a patient is taking duplicate medication, when the medication is outside a particular range, when the patient is taking contradicting medication, and when the patient is taking medication that can create allergies.

According to alternative embodiments, the patient data management platform can generate checklists that can be used for assessment during a visit at a patient's house. For example, the checklist can target a home assessment or a fall assessment, e.g., the CDC Stopping Elderly Accidents, Deaths & Injuries (STEADI) assessment. The checklist can be displayed directly at a paramedic mobile device and the paramedic can complete the checklist with the patient during the visit.

According to alternative embodiments, the patient data management platform can enable integration to a billing system. For example, the platform can extract billing information, e.g., for a particular visit, patient, neighborhood, and enter it to a billing system. The billing information can be used for setting up payments of the paramedic services, for example, by Medicare, Medicaid, and commercial insurance. In addition, the platform can allow integration to a Health Level 7 Information Standards (HL7) system with a health information exchange (HIE). The HL7 integration can enable sharing data between hospital systems, as well as other HIEs.

According to alternative embodiments, the patient data management platform can support evaluation of different community paramedicine systems based on various performance measures. The performance measures can include, for example, the number of readmissions to a hospital of a patient who is enrolled in a paramedicine system, the number of 911 calls placed by the particular patient, and the number of emergency room visits for the particular patient. Such performance measures may be measured across a set of patients and/or across a community, and the goals of a community in implementing a community paramedicine platform or system may be referred to as community goals. Community goals may include, without limitation, reducing the hospital readmission rate for a set of patients (e.g. a community) over a particular time period (e.g. a year), and/or reducing the frequency and/or extent of use of emergency medical services by a set of patients (e.g. a community) over a particular time period (e.g. a year). The options for the patient-specific goals that the platform supports may be in furtherance of such community goals. For example, preventing hospital readmission rates for congestive heart failure patients within thirty days of discharge is an example of a patient-specific goal (trackable by the platform) which is in furtherance of the community goal of reducing the hospital readmission rate for the patient's community over the course of the year. The platform can also provide comparative statistics for the performance measures, for example, comparing the patient behavior regarding hospital re-admissions, 911 calls, and emergency room visits, before and after the patient has joined the paramedicine system.

According to some embodiments, the patient data management system or platform is a "cloud-based" or server-based platform that allows communities, health care providers, patients, and/or other users to track information about program types, program status, and/or program goals for a number of users in a seamless and instantaneous fashion that would not be possible using traditional patient record paperwork methodologies. For example, the patient data management system according to some embodiments of the present disclosure can instantly determine whether the patient being visited is part of a program, compare information for the current visit with one or more prior visits, alert the caregiver to inconsistencies and/or helpful information (e.g. noted allergies, or discrepancies in medication information provided in subsequent visits), and permit monitoring of the patient's progress toward a particular goal and/or toward a particular goal over a particular time period, despite the fact that the patient is visited at different times, sometimes by different health care providers. The patient data management system is thus also able to monitor and provide benefit from visits among hundreds or thousands of patients over long periods of time. Furthermore, the server-based platform permits users to engage with the platform using a variety of different devices, for example by permitting engagement with the platform via a web browser interface, thereby harmonizing use of the system among a variety of different users and a variety of different devices in a manner that would not be possible with traditional, personal pen-and-paper records management.

As used herein, "health care provider" is used in its broadest sense to refer to someone who is able to evaluate a patient and/or treat a patient, including without limitation non-medical evaluation and non-prescription treatments. For example, a health care provider can be a non-medical member of the community who has been trained to use the patient data management system or platform. In other cases, a health care provider may be a paramedic, an EMS technician, and/or an employee of a company that provides health care services. The platform or system according to embodiments of the present disclosure may be used by users other than or in addition to health care providers. The platform or system according to embodiments of the present disclosure may be used by patients.

As illustrated in FIG. 1, a patient data management system or platform 100 according to embodiments of the present disclosure performs the functions, e.g., community paramedicine functions, described herein. System 100 can include a mobile environment 101, an enterprise environment 102, and an administration environment 103. Devices within the various environments 101, 102, 103 may be communicably coupled via a network 120, such as, for example, the Internet.

The patient data management platform may be a web-based or cloud-based system and interface hosted by the enterprise application server 128 and/or the enterprise storage server 126, and may be implemented by software or other instructions contained in a computer readable medium and executed by a processor on servers 126, 128, or elsewhere. The patient data management platform may be accessed with a computing device, for example a mobile computing device 108 and/or by an enterprise user 124 with a fixed or stationary workstation 122. According to some embodiments, the patient data management platform is adapted to be accessed and used by a user, such as for example an EMS technician, nurse, or paramedic 114, upon a login (e.g., username and password) or other authentication or security check. References herein to user 114 or paramedic 114 are also references applicable to other users, including without limitation paramedics, EMS technicians, clinicians, nurses, physicians, and any other type of health care provider or user. According to some embodiments, the patient data management platform is web-based and may be accessed by one or more common web browsers, without the pre-installation of any non-browser-based or customized software on the mobile computing device 108 or workstation 122. The mobile computing device 108, workstation 122, and servers 126, 128 are communicably coupled via network 120. Such communicable coupling may be wired, wireless, or via some other coupling that permits information or data to be sent and/or received.

The mobile computing device 108 can be any computing device, for example, a tablet, laptop, computer, personal data assistant, smart phone, or touchscreen device. Such a device 108 is capable of being carried by the paramedic 114 when the paramedic 114 visits the patient 116, according to some embodiments. The term "visit" is used in its broadest sense to refer to an encounter, whether real or electronic or telephonic, and is not limited to an encounter resulting from a healthcare provider traveling to a patient location. The mobile computing device 108 can be communicably coupled to other medical devices 106, for example a portable defibrillator, or other devices as described herein. Such other medical devices 106 may be communicably coupled directly with mobile computing device 108, and/or communicably coupled indirectly with mobile computing device 108 via network 120 and/or servers 126, 128. The mobile computing device 108 may include a computer readable medium 118, such as a database. The servers 126, 128 may include another computer readable medium 130, such as a database. The instructions for performing the functions described and/or shown herein may be included on one database 118, 130, or may be included on other databases (not shown), or may be distributed across multiple databases including those shown and those not shown. In addition, the processors, computers, or workstations described herein may be a single processor or processor bank, or may be multiple processors working simultaneously or at different times to execute instructions to perform the functions associated with the patient data management platform and user interfaces as described herein. For example, the database 130 may be or include a medical information database, but such medical information database may also be on or partially on database 118 or other databases. This is consistent with the patient data management platform being wholly or partially cloud-based, according to some embodiments.

Figure 2:
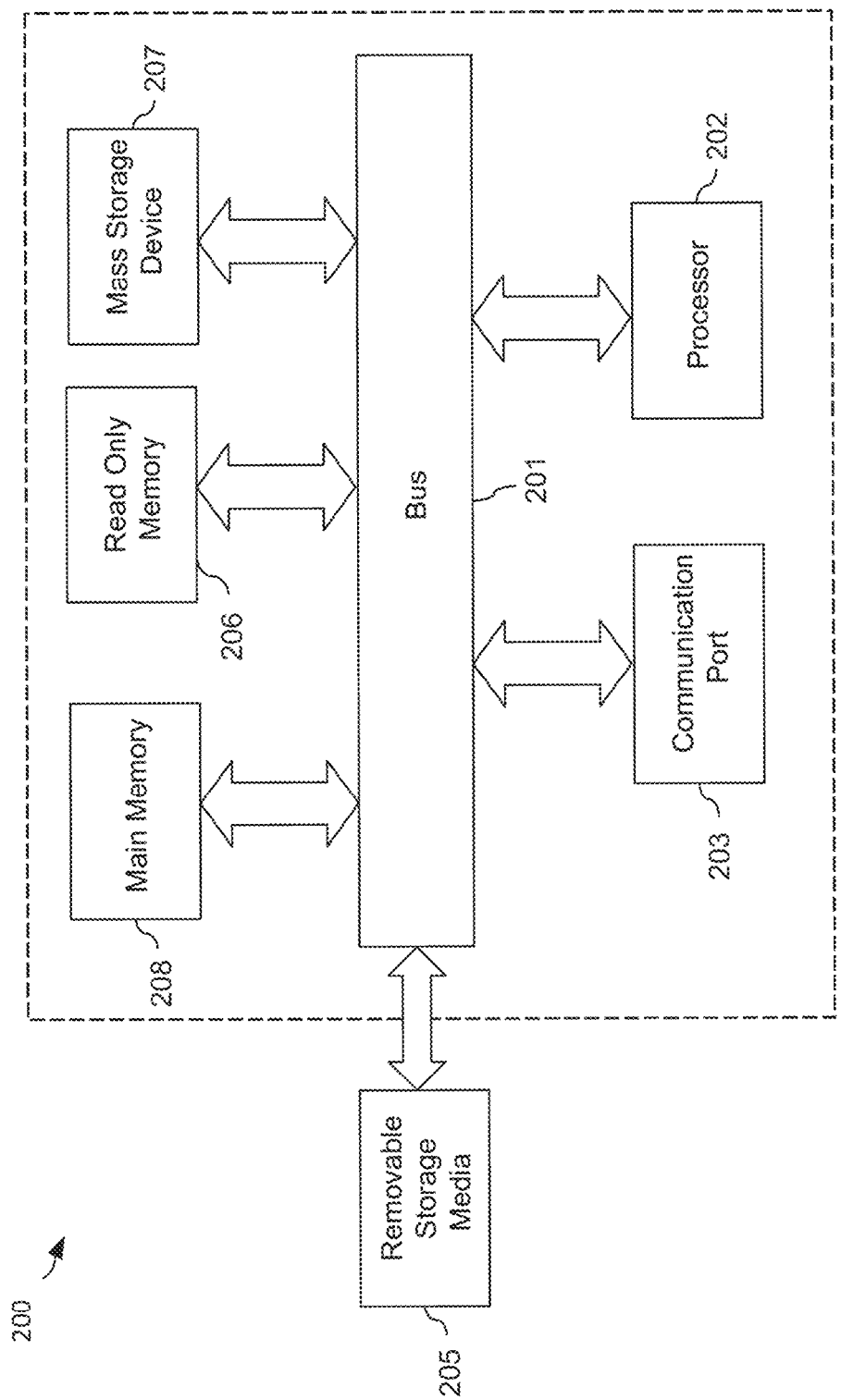
FIG. 2 illustrates a computer system, according to embodiments of the present disclosure.

FIG. 2 illustrates an exemplary computer platform, including a processor 202 and other hardware which may be used to implement the functionality described herein. For example, any one or more of the components illustrated in FIG. 1 may incorporate, or be incorporated within, a computer system 200, according to embodiments of the present disclosure. According to the present example, the computer system includes a bus 201, at least one processor 202, at least one communication port 203, a main memory 208, a removable storage media 205, a read only memory 206, and a mass storage 207.

Processor(s) 202 can be any known processor, or any known microprocessor or processor for a mobile device. Communication port(s) 203 can be, for example, any of an RS-232 port for use with a modem based dialup connection, a copper or fiber 10/100/1000 Ethernet port, or a Bluetooth® or WiFi interface, and/or an infrared port, or combination of those. Communication port(s) 203 may be chosen depending on a network such a Local Area Network (LAN), Wide Area Network (WAN), or any network to which the computer system 200 connects. Main memory 208 can be Random Access Memory (RAM), or any other dynamic storage device(s) commonly known to one of ordinary skill in the art. Read Only Memory (ROM) 206 can be any static storage device(s) such as Programmable Read Only Memory (PROM) chips for storing static information such as instructions for processor 202, for example.

Mass storage 207 can be used to store information and instructions. For example, flash memory or other storage media can be used, including removable or dedicated memory in a mobile or portable device, according to embodiments of the present invention. As another example, hard disks such as SCSI drives, an optical disc, an array of disks such as RAID, or any other mass storage devices can be used. Bus 201 communicably couples processor(s) 202 with the other memory, storage and communication blocks. Bus 201 can be a PCI/PCI-X or SCSI based system bus depending on the storage devices used, for example. Removable storage media 205 can be any kind of external hard-drives, floppy drives, flash drives, zip drives, compact disc-read only memory (CD-ROM), compact disc-re-writable (CD-RW), or digital video disk-read only memory (DVD-ROM), for example. The components described above are meant to exemplify some types of possibilities. In no way should the aforementioned examples limit the scope of the invention, as they are only exemplary embodiments of computer system 200 and related components; numerous other computer hardware and/or firmware components are contemplated by the present disclosure.

Data from the device 108 (and therefore data from the devices communicably coupled with the device 108) can be received by one or more enterprise storage servers 126 in an administration environment 103 and stored in an enterprise database 130, and the same information may be accessed and provided by one or more enterprise application servers 128 to a workstation 122 of an enterprise user 124, according to embodiments of the present disclosure.

Figure 3:
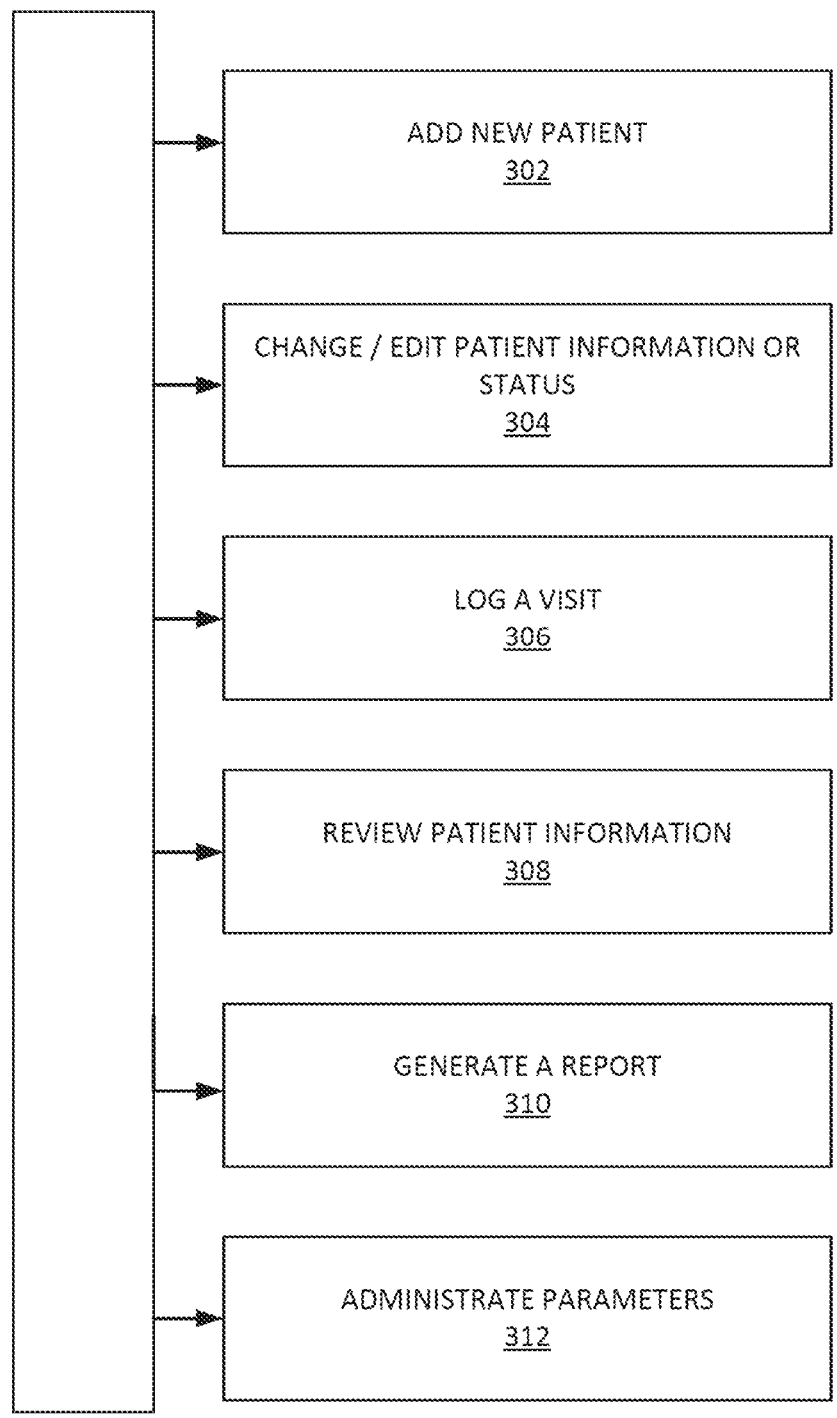
FIG. 3 illustrates a set of capabilities of a patient data management system, according to embodiments of the present disclosure.

FIG. 3 illustrates high-level groupings or modules of functions performed by the patient data management system 100, according to embodiments of the present disclosure. System 100 permits new patients to be added (module 302), patient information or status to be changed (module 304), visits to be logged (module 306), patient information to be reviewed (module 308), reports to be generated (module 310), and system parameters to be administrated (module 312). As described in greater detail herein, such modules 302, 304, 306, 308, 310, and 312 may include functionalities and subroutines that are specific to community paramedicine, mobile integrative heath or EMS mobile health programs or services, and which are typically not included or not needed in systems for tracking traditional EMS encounters, including but not limited to medication reconciliation, data entry parameter alerts, and narrative entry fields related to goals, patient assessment, and patient plans (e.g., "SOAP" patient documentation). The screen shots shown and described herein illustrate examples of data fields for which the health care provider, e.g., a paramedic, user 114 may be prompted on device 108, collected by device 108 and sent to server 126 and/or 128, and stored in a medical information database 130.

Although certain exemplary data fields, ranges, and values are discussed, one of ordinary skill in the art will appreciate, based on the present disclosure, that other data fields, ranges, and/or values may be used, collected, transmitted, and/or stored by system 100, for example in furtherance of other community paramedicine or mobile integrative health goals or patient programs.

FIGS. 4-31 illustrate screen shots from a user interface of an exemplary patient data management platform, according to embodiments of the present disclosure. The exemplary patient data management platform shown in these screen shots is a community paramedicine platform, but could be any of the other platforms or systems discussed herein. FIG. 4 illustrates a portal screen into a community paramedicine platform. FIG. 4 shows other applications available from the same provider (e.g., ZOLL Data Systems), and clicking on the "EMS Mobile Health" option 401 takes the user to the screen of FIG. 5. FIG. 5 illustrates a patient listing 402 for the community paramedicine platform, which lists, for example, the patient's name, date of birth, age, sex, phone number, date of last visit, number of visits, program type, and program status.

This listing can be sorted or filtered according to one or more of the columns. Clicking on or selecting the add a patient link 403 takes the user to the screen of FIGS. 25 and 26, and clicking on or selecting the view patient list for all products link takes the user to the screen of FIG. 30. As used herein, "clicking," "clicking on," "selecting," and "choosing" are used interchangeably to refer to a user's action, by whatever mechanism, for activating a link associated with a portion of the user interface, including by touching the link on a touch screen interface, clicking or double clicking with a mouse, or using audio or visual prompts or selections. Clicking on the patient name 405 takes the user to the screen of FIG. 6, which provides a patient overview for the selected patient.

Figure 6:
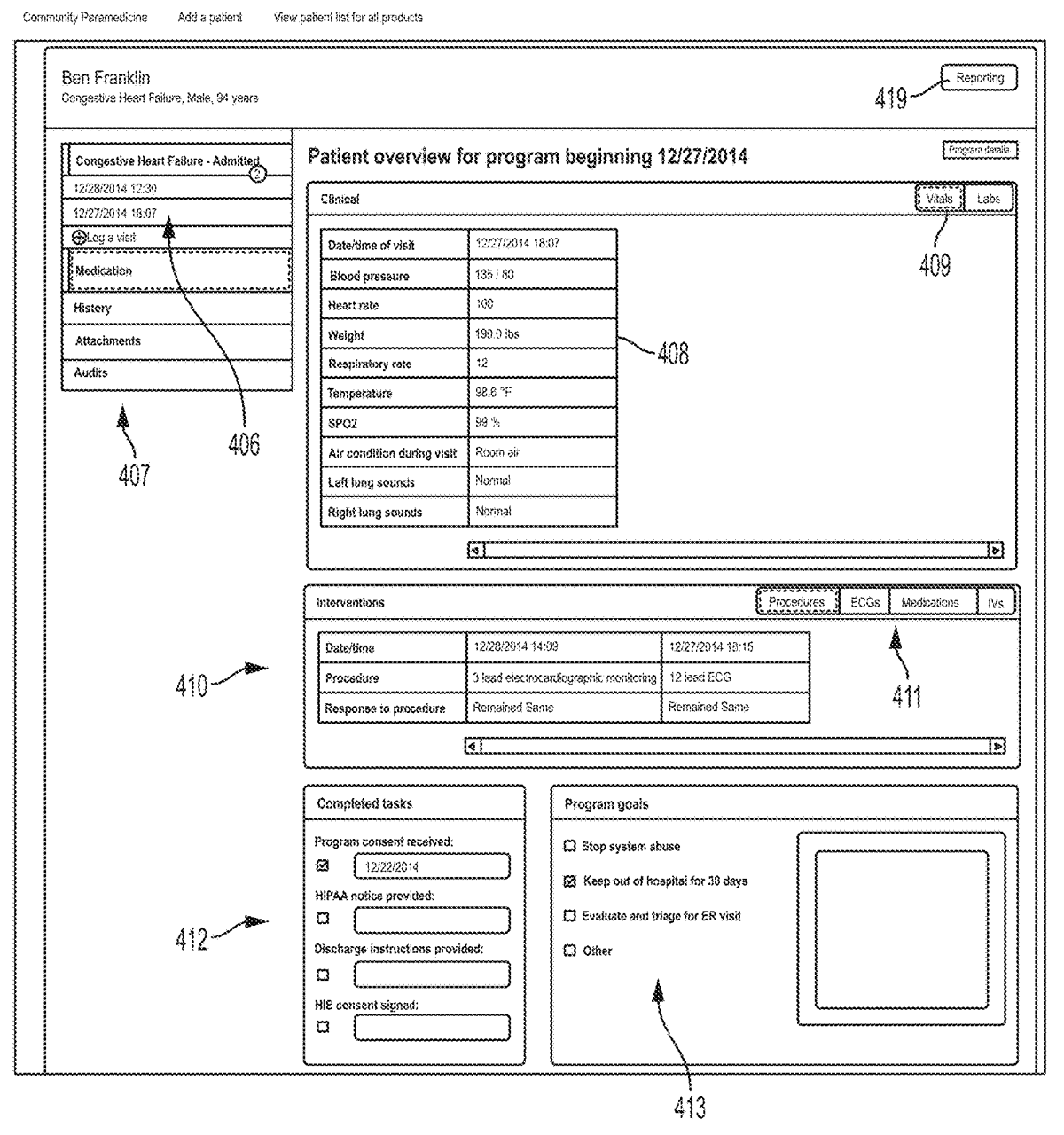

As shown in FIG. 6, the patient overview may include a portion 406 listing prior visits logged to the patient (e.g., by date), a patient information portion 407 with links to information about the patient (e.g., medication, history, attachments, and audits), a clinical summary portion 408 including clinical information from prior visits, which may be toggled between various sets of information, for example vital sign information and lab information, using buttons 409. The overview may include an interventions portion 410 which may be toggled between procedures, ECGs, medications, and IVs using buttons 411. The overview may further include a completed tasks portion 412 and a program goals portion 413, as shown, according to embodiments of the present disclosure. A small number (e.g., "2") in the portion 406 may indicate the total number of visits logged, even when the visit dates are not listed in portion 406, according to some embodiments.

Figure 7:
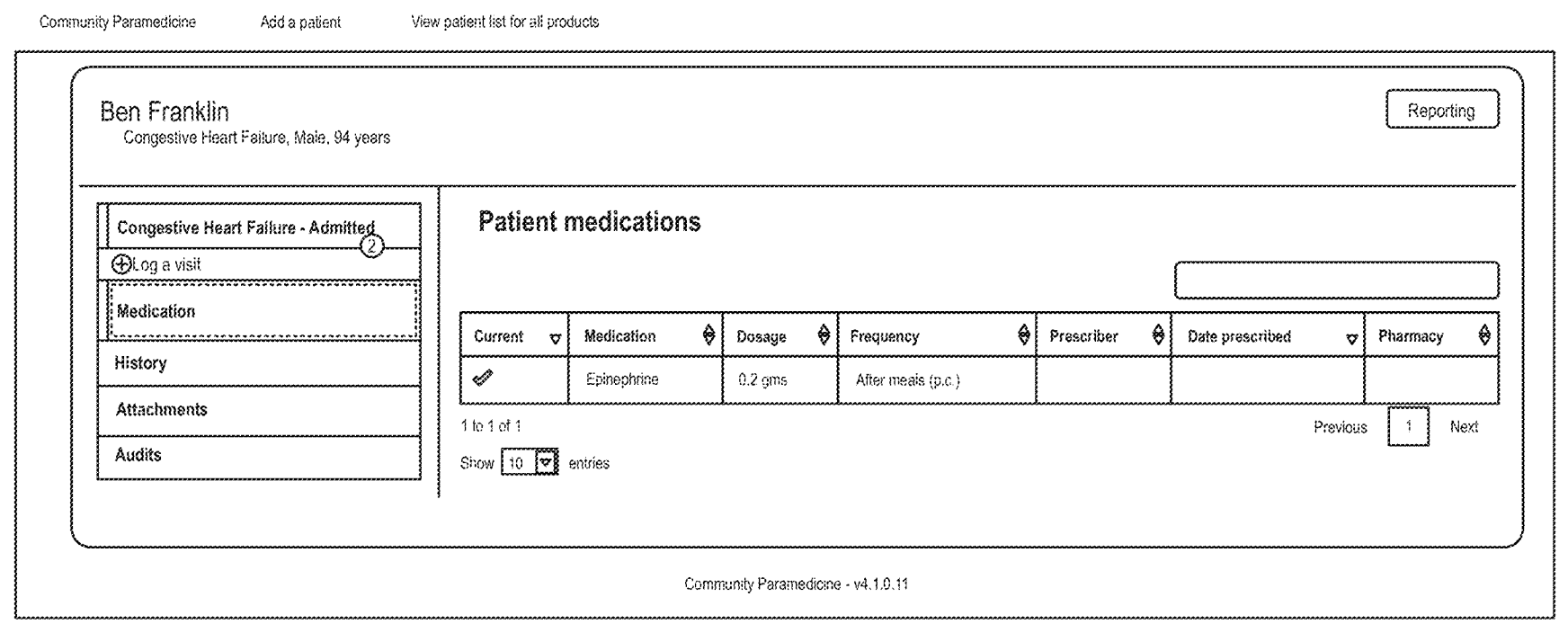

Selecting the "medication" link in the patient information portion 407 takes the user to the screen of FIG. 7, which lists the patient's medications as entered upon patient setup or during visits. This may include the name of the medication, the dosage, the frequency, the prescriber, the date prescribed, the pharmacy, and/or an indication of whether the medication is currently being taken. According to some embodiments of the present disclosure, the medication information displayed on the screen of FIG. 7 is "read-only," or non-editable. Medication information may be edited by logging a visit, as described below, or editing a patient's information, as described below, according to some embodiments of the present disclosure.

Selecting the "history" link from the patient information portion 407 takes the user to the screen of FIG. 8, which includes a medical history portion, a medication allergies portion, a food/environmental allergies portion, and a social history portion. One or more such portions may include data fields or selections auto-populated into a drop-down or list selection format, for example as shown permitting an item from the one column (e.g., the left-side column) to be "added" or "deleted" from the patient-specific column (e.g., the right-side column). Other portions, for example the social history portion, may include fields that permit the entry of text-based narrative. Because this information is patient-specific but not limited to a particular visit, such history may be edited on the screen of FIG. 8 rather than in the patient visit log process, according to some embodiments. The available fields for one or more of the information portions may be autopopulated using a standard list or a predefined list. For example, the medical history selections may include items set forth in the ICD-10 standard, the medication allergies selections may include items set forth in the RxNorm standard, and the food/environmental allergies selections may include items set forth in the SNOMED standard.

Figure 9:
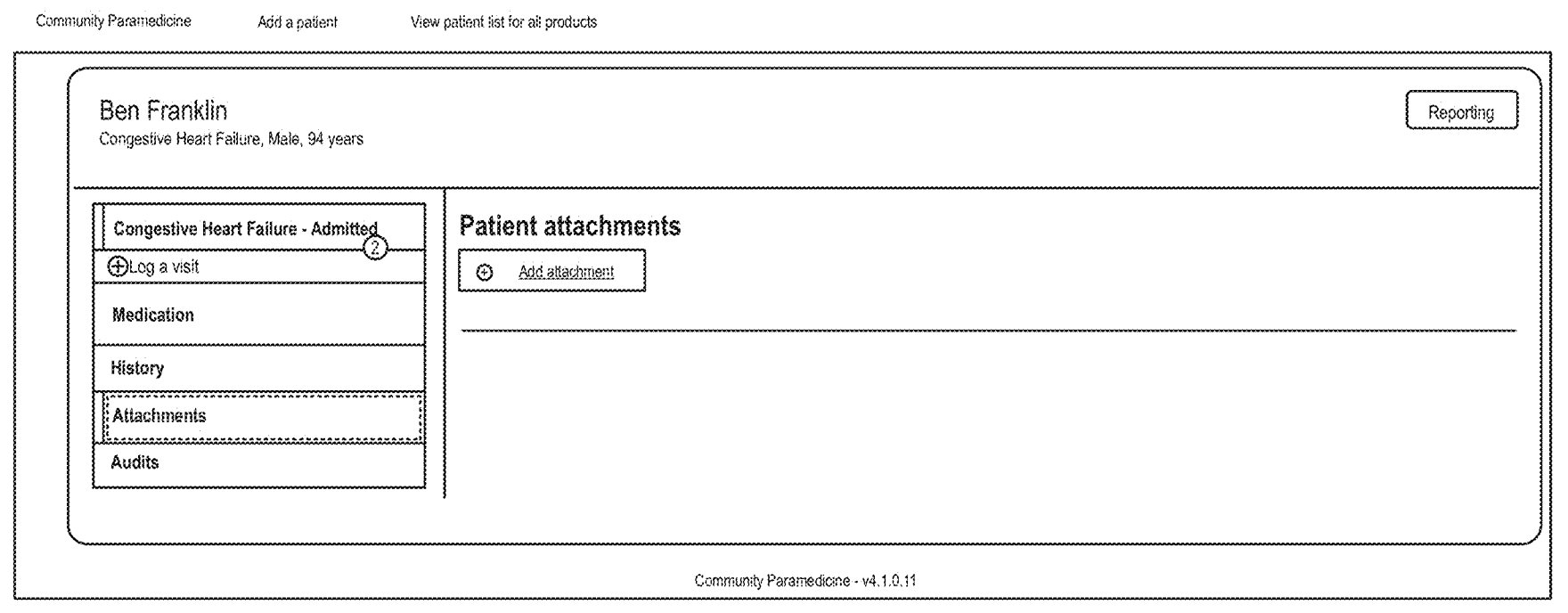

Selecting the "attachments" link from the patient information portion 407 takes the user to the screen of FIG. 9, which shows any patient attachments and permits the user to upload additional attachments that are associated with the patient by using the "Add attachment" link. Attachments that may be uploaded include, for example, image files associated with ECGs or x-rays or ultrasounds or MRIs, consent forms, discharge instructions, survey results, and/or patient signatures or consent documentation. Such attachments may be associated with a date, to permit the user of the community paramedicine platform or system to see images that help paint the picture of the patient's medical history or information from prior encounters or visits.

Selecting the "audits" link from the patient information portion 407 takes the user to the screen of FIG. 10, which shows which actions have been taken to edit or modify information about the patient, including for example the date and time of the action, the type of action or identification thereof, the user who made the edit, and the details or comments regarding the change to the patient information. Such an audit trail provides information useful in compliance and auditing of the community paramedicine system and/or particular patients and their care and treatment. According to some embodiments, the audit information may be provided in "read-only" or non-editable fashion. According to some embodiments, the information available in or accessible by the audits screen of FIG. 10 may be used to help various agencies or companies ensure that their patient interactions and their platforms are compliant with the Health Insurance Portability and Accountability Act ("HIPAA").

Selecting the "log a visit" link from the portion 406 takes the user to the screen of FIG. 11. From this screen, the user may log a visit, aided by the navigation tabs 414. The screen of FIG. 11 shows patient visit navigation tabs including, for example, "log a visit," "medications," "vitals," "labs," "interventions," and "narrative." Because not all types of information are or need to be entered for each patient visit, the user can navigate through the visit logging interface either by using the "next" buttons 415, or by clicking directly on one of the navigational tabs 414 to go directly to the particular type of data entry associated with the visit, according to some embodiments of the present disclosure. Other buttons appearing on each of the patient logging pages include "save" and "cancel," which permit the user to save the visit logged so far, or cancel the visit log that had been generated.

Figure 12:
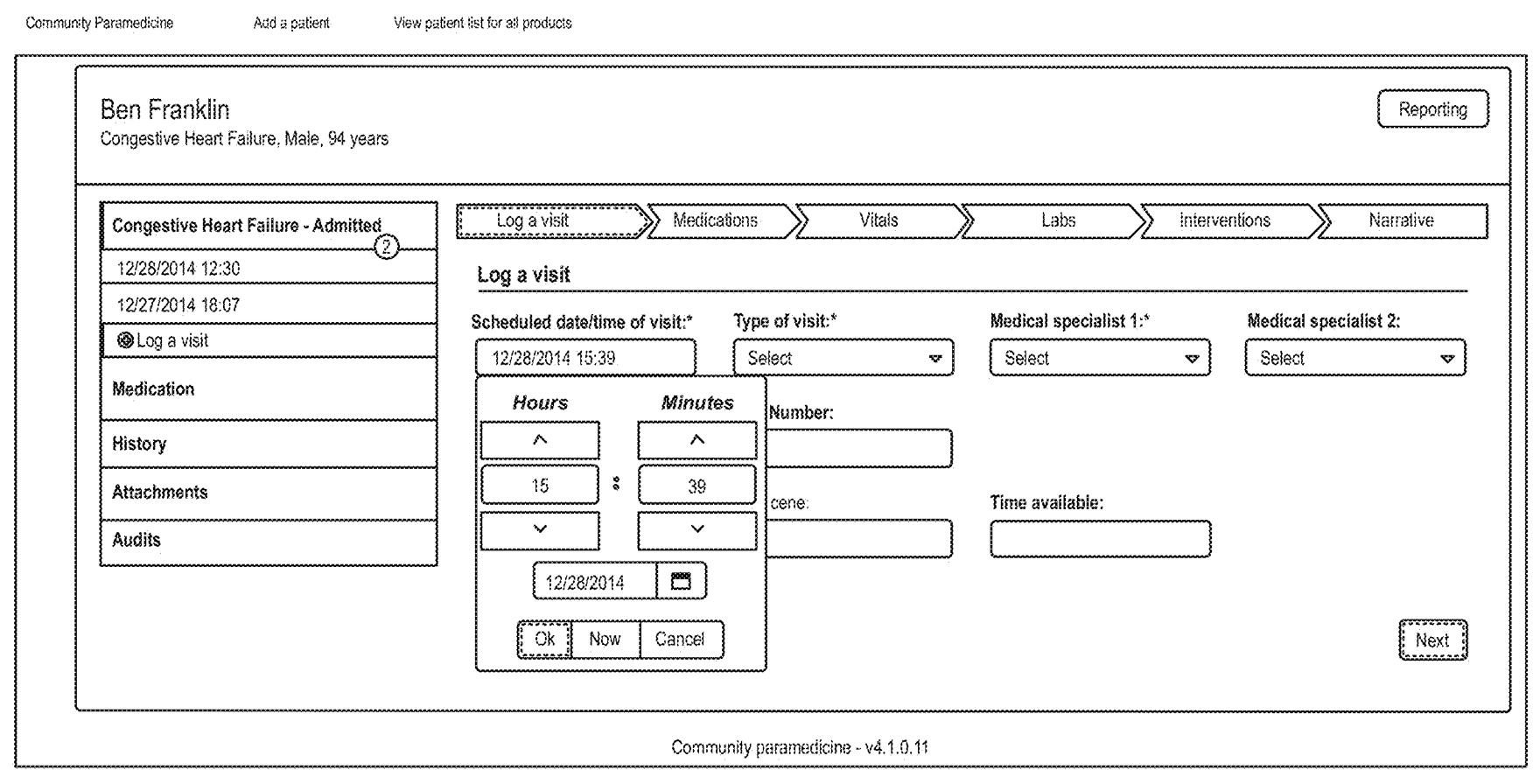

The initial visit logging page, shown in FIG. 11, permits the user to enter information about the scheduled time and type of visit, the medical specialists (e.g., paramedics, doctors, EMS technicians, and the like) visiting the patient, the vehicle (e.g., the ambulance or other vehicle) used to visit the patient, the run number, the en route time, the on scene time, and the time available. Such data may be entered manually, and/or all or portions of such data may be entered or received automatically, for example from an EMS navigation or dispatch or computer-aided dispatch system, which may include other devices or systems communicably coupled to the mobile computing device 108 either directly or indirectly, according to embodiments of the present disclosure. As shown in FIG. 12, fields such as those which ask for dates and/or times may include an auto-popup feature that facilitates time entry with an hour and minute incremental arrows, a calendar, and/or selectable buttons that include "ok," "now," and "cancel" as shown.

Figure 13:
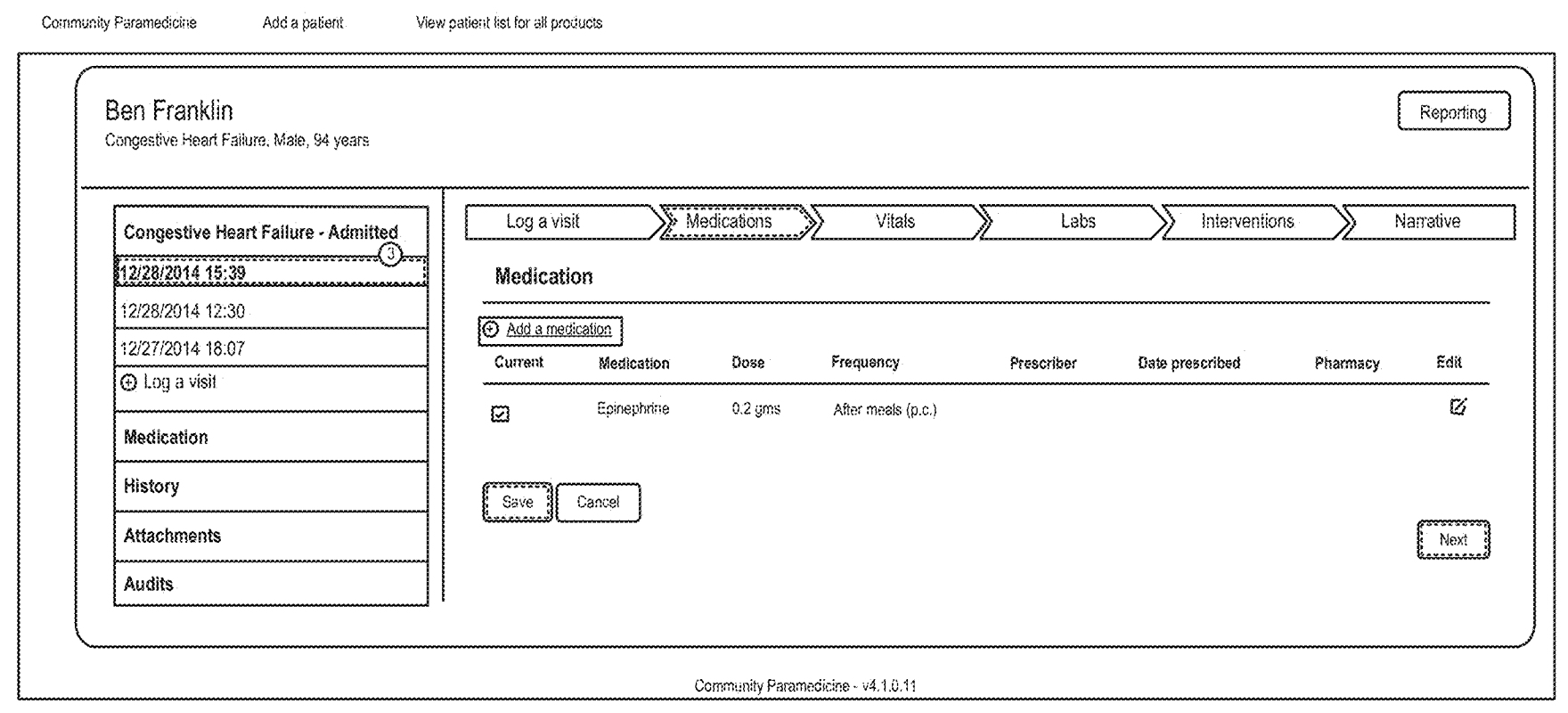

Proceeding to the medication tab of the patient visit log, shown in the screen shot of FIG. 13, the user is shown a list of medications which the patient is known to take (based on information entered previously and/or during the addition of the patient to the community paramedicine system). This screen permits medications to be added, and also permits medications to be edited based on new information from the patient. In this way, the community paramedicine system 100 queries a medical information database, e.g., 130 (see FIG. 1), to send to the mobile computing device 108 a list of patient medications, thereby permitting the user 114 to reconcile the list of patient medications with the list of medications obtained during the patient visit that is being logged, for example the list of medications which the patient shows to the paramedic or tells the paramedic are being taken. The medication information may include information similar to that obtained or viewed by clicking on the "medication" link from the patient information portion 107. This reconciling of patient medication information with existing data improves patient care and accuracy of documentation, according to some embodiments. Medications available to be logged or added may be selectable from an administrator-selected set or subset of the RxNorm standard list, for example. During the visit logging process, a medication listed as a current medication may be edited (e.g., by the user selecting the "edit" link) and indicating in the community paramedicine database that the particular medication is "discontinued" or no longer current for the particular patient. The medication reconciliation process as described and/or shown herein assists in ensuring that the patient is taking the correct medications in the correct dosages for the patient's condition, and assists in identifying potentially negative or costly medication errors, according to some embodiments of the present disclosure.

Figures 14, 15, 16:
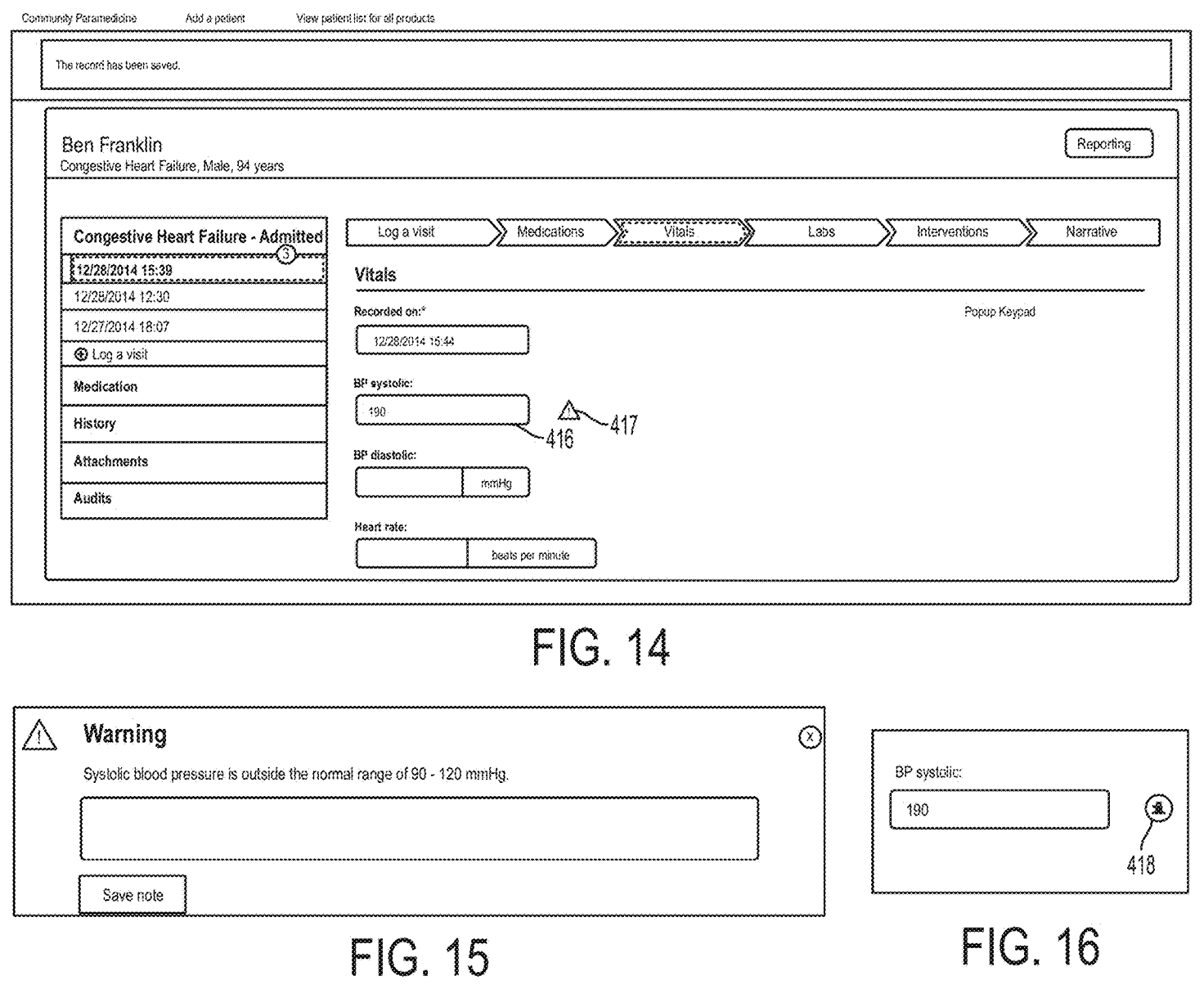

Proceeding to the "vitals" navigation tab of the patient visit log, shown in the screen shots of FIG. 17, permits the patient's vital signs to be entered. Such vital signs may include, for example, the date and/or time on which the vital signs were recorded (including a facilitating window similar to that shown in FIG. 12), the systolic and diastolic blood pressure values, heart rate, weight, respiratory rate, temperature, SpO2, air condition during SpO2 test, whether supplemental oxygen was being used, left lung sounds, right lung sounds, and/or narrative regarding lung sound notes, according to some embodiments. As illustrated in FIGS. 14, 15, and 16, the community paramedicine platform may include a form of data verification and alerting based on values entered. While an example is described with respect to the systolic blood pressure value, such data verification and alerting may be used for other fields or values, including numeric and non-numeric values (e.g., if "left lung sounds" were other than "normal," the user may be alerted and or prompted as described herein).

As shown in FIG. 14, the user enters a systolic blood pressure value of 190 at box 416. The community paramedicine system compares the entered value with a predetermined value or range of values and determines that the entered value is outside of the predetermined value or range of values, and displays an alert icon 417. Along with or subsequent to the display of the alert icon 417, the community paramedicine interface pops up a dialog box, as shown in FIG. 15, informing the user that the systolic blood pressure is outside of the normal range of 90-120 mmHg (or whatever the predetermined value or range may be), and includes a data entry field for the entry of a note. The user may enter and save a note regarding the higher than normal systolic blood pressure, and then instead of the alert icon 417, the text box 416 for that value will display an informational icon 418 next to it, the clicking of which displays the warning and/or the previously-entered note.

Figure 18:
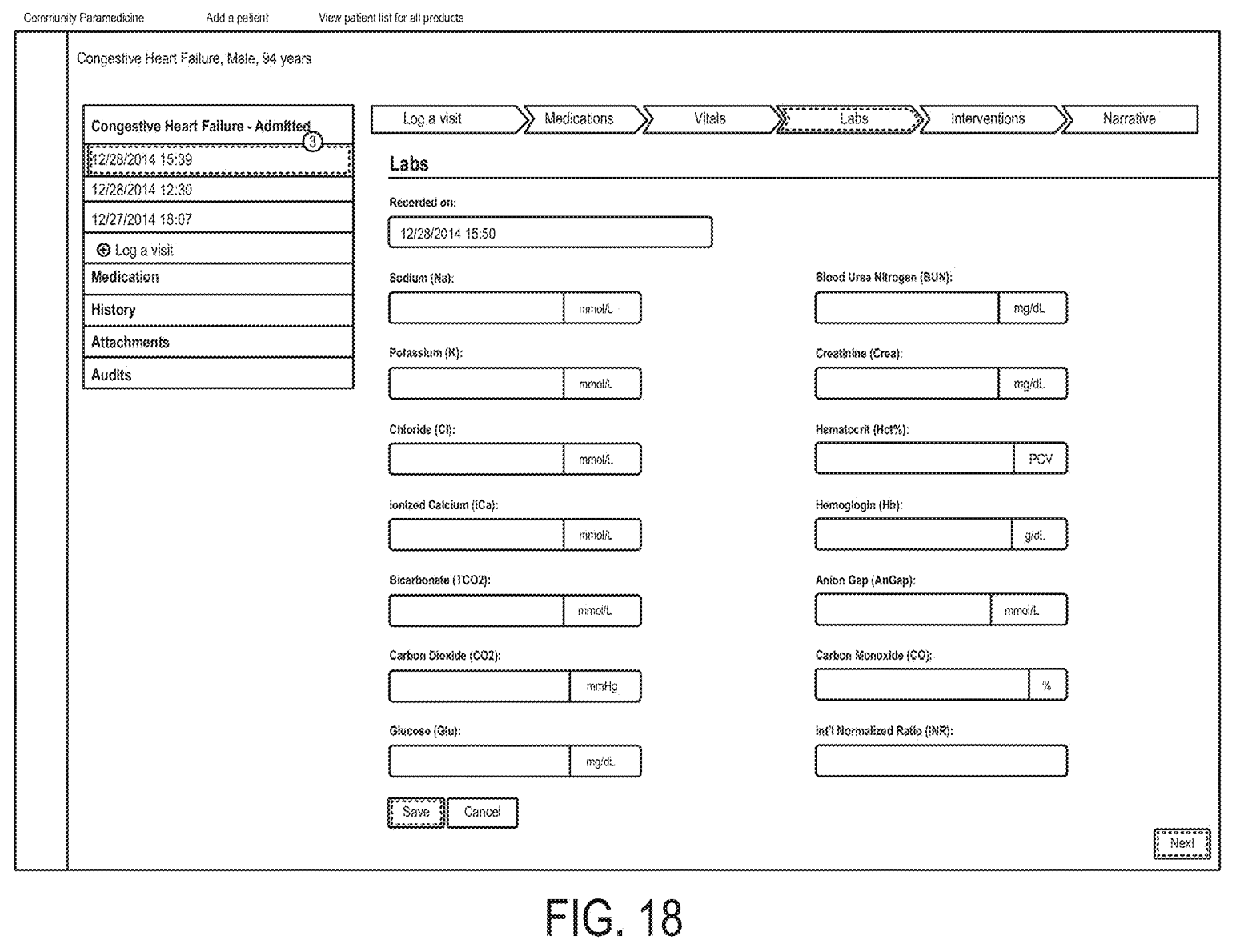

FIG. 18 illustrates the screen associated with the "labs" navigation tab for the patient visit logging selection. This screen collects various lab results from the user along with the date such results were recorded. Modern mobile medical technology permits such "lab" tests to be conducted on the patient or the patient's tissues or tissue samples at the site of the visit (e.g., the patient's home), for example with devices that are coupled to the patient and/or which receive or contact tissue or blood samples of the patient. Various lab devices, e.g., an i-STAT® or like devices, may be communicably coupled to the mobile computing device 108 to permit automatic data entry, and/or such values may be observed and entered manually. Such data entry fields may also include data verification and alerting, as described above. According to one example, the fields available for input may include one or more of sodium level, potassium level, chloride level, ionized calcium level, bicarbonate level, carbon dioxide level, glucose level, blood urea nitrogen level, creatinine level, hematocrit level, hemoglobin level, anion gap, carbon monoxide level, and international normalized ratio value. One of ordinary skill in the art, based on the present disclosure, will appreciate that the types of data which the patient data management platform 100 is capable of recording about the patient or a patient visit, or for which the patient data management platform 100 prompts a user 114 to enter, or the order or manner of such prompting or recording, may vary widely to include a subset of, each of, and/or more than those values or parameters shown or described herein, according to embodiments of the present disclosure. This includes vital sign and lab data values, as well as other fields of the patient data management platform or system 100.

Figure 19:
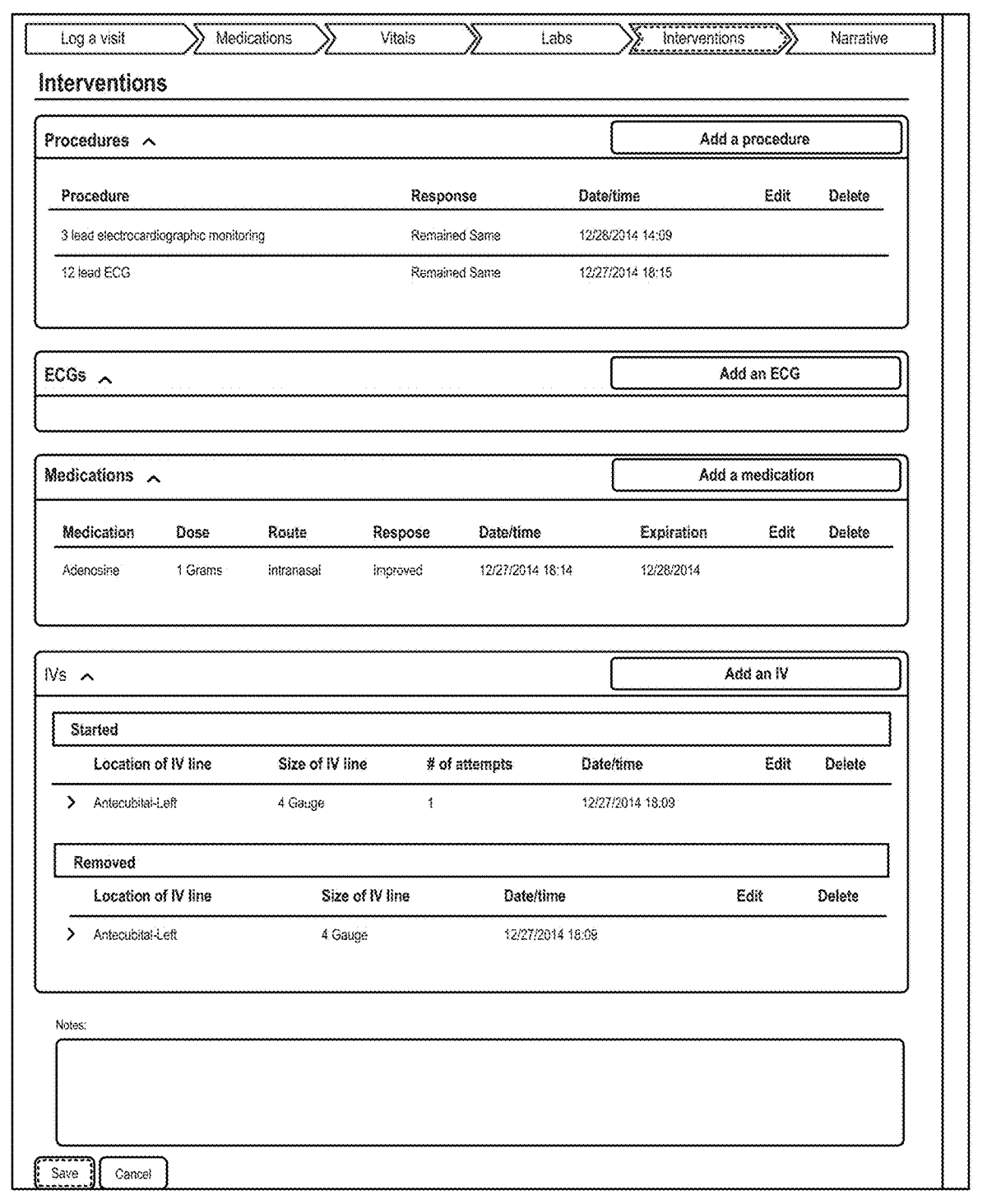

FIG. 19 illustrates the screen associated with the "interventions" navigation tab for the logging of the patient visit. The screen of FIG. 19 includes a procedures portion listing prior procedures performed on the patent by procedure type, response notes, and date/time, and permits additional procedures to be added with an "add procedure" link. The screen of FIG. 19 further includes an ECGs portion, where prior electrocardiograms are listed and new ECGs may be added with the "add an ECG" link or automatically uploaded from a monitor or other device. The screen of FIG. 19 further includes a medications portion which lists prior medications administered to the patient (e.g., on a prior visit), and permits new medications to be added with the "add a medication" link. The screen of FIG. 19 further includes an IVs portion which lists prior IV lines, their locations, size, number of attempts, date/time they were started, and date/time they were removed, and permits IV notations to be added with the "add an IV" link. The screen of FIG. 19 further includes a notes portion permitting the user to enter notes about patient interventions. Thus, the screen of FIG. 19 permits the user, for example the paramedic 114, to note any patient interventions made during the patient visit being logged, and to see prior interventions in order to take into account the historical picture of the patient's health and interventions and reconcile the prior interventions with the current interventions. For example, the user might see under "medications" that the administration of aspirin two days ago resulted in a response of "improved," and use such information in deciding to administer aspirin again under similar circumstances encountered on the visit being logged. This functionality not only improves accuracy of patient charting, but it also results in less data entry errors and potentially better decision making by the paramedic. In some embodiments, the user is able to edit or delete interventions for the visit being logged, but not interventions logged in prior visits or by others. In some embodiments, only the user that logged a visit can edit the editable information for such visit.

Figure 21:
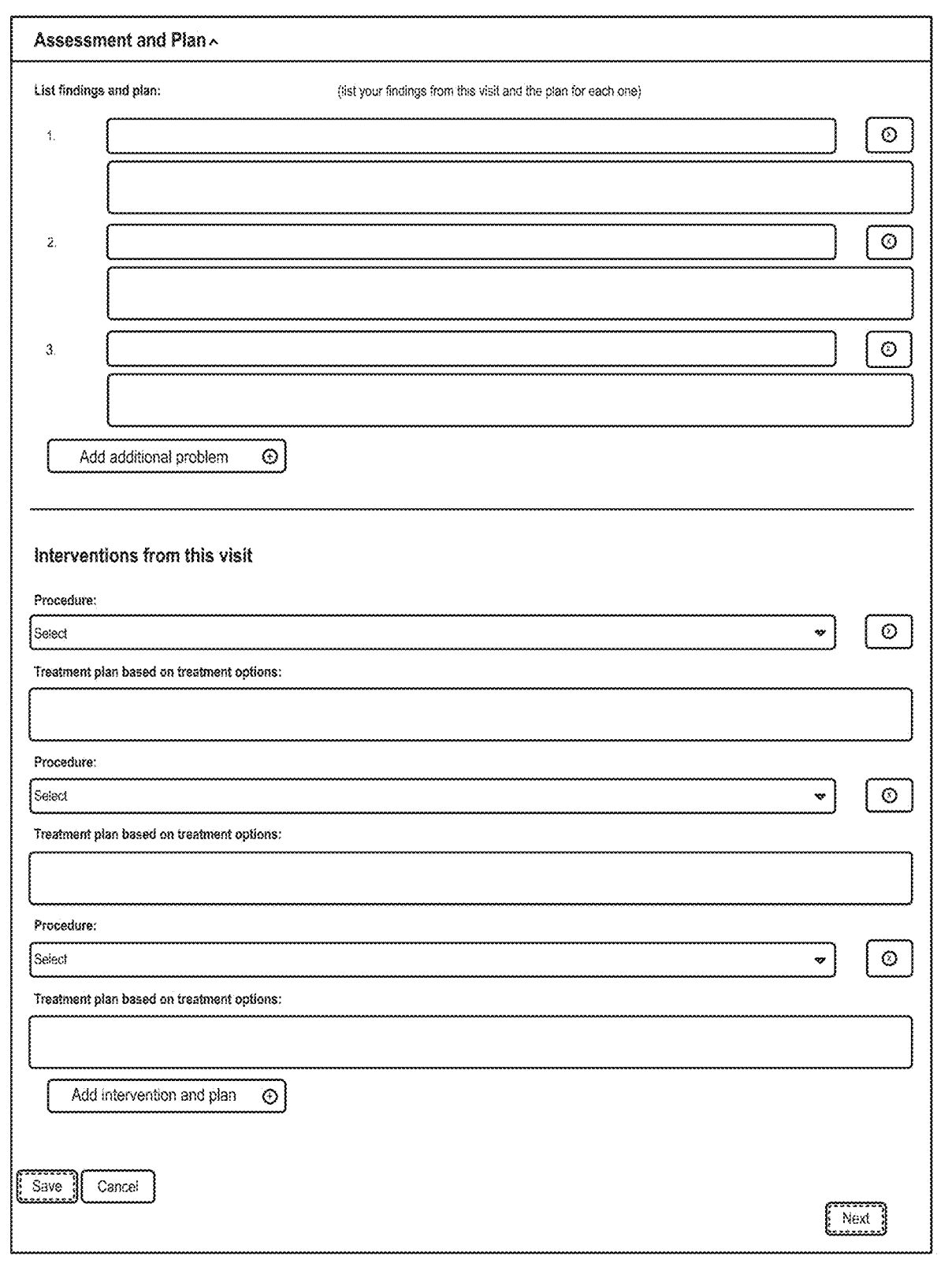

FIG. 20 illustrates a top portion and FIG. 21 illustrates a bottom portion of a screen (which may be included on a single screen or separated on two or more screens or viewable by scrolling) for the "narrative" tab of the patient visit logging module. The patient narrative screen includes a description of the "program type", as well as a subjective portion with user input features that permit the user to describe the patient and the patient's medical condition and how the patient's condition has changed since the last visit; an objective portion with user input features that permit the user to describe significant exam findings and additional findings such as labs or 12-lead ECGs; and an assessment and plan portion where findings may be listed along with narrative descriptions of the plan for each finding. Such narrative input fields permit the user, for example the paramedic 114, to enter narrative data according to a desired format. In this example, the format is a modified "SOAP" format: subjective, objective, assessment, and plan format. Other formats for entry of narrative data relating to the non-emergency medical visit may be used, including without limitation a traditional "SOAP" format which differs from the modified "SOAP" format shown. Additional patient problems may be identified using the "add additional problem" link. As shown on FIG. 21, the narrative screen may also include a portion listing some or all interventions from the current visit, for example a procedure selection and a narrative input box for a treatment plan based on treatment options for each procedure selection. Additional interventions and plans may be added using the "add intervention and plan" link. In some embodiments, the interventions logged with the "interventions" navigation tab for the same visit (see for example FIG. 19) may be automatically populated in the "narrative" screen shown in FIGS. 20 and 21, along with text boxes to permit the user to enter narrative about the logged interventions.

Once the patient visit has been logged, the user may select the "save" or "next" link until the visit log process is complete and the visit has been logged. The logged visit will then appear in the patient visit log portion 406 of the screen of FIG. 6, for example. Clicking on one of the dates of the patient visit log permits users to be guided through the same navigational tabs described with respect to FIGS. 11-21, but some or all of the data fields will be viewable but not editable, according to some embodiments. In other embodiments, such data is editable but an audit trail is created to track any edits, and such data may be accessible via the "audits" link selection from the screen of FIG. 6, for example.

Figure 22:
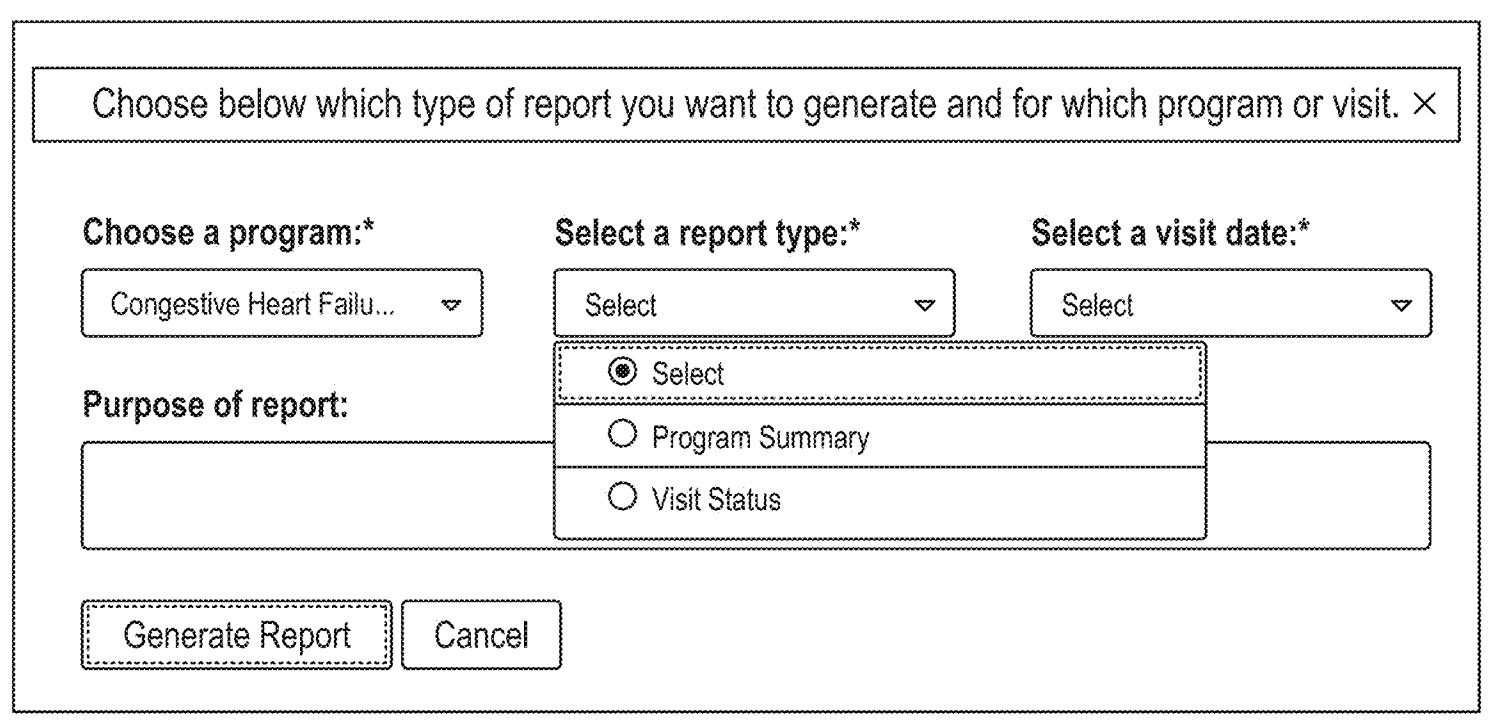

Selecting the reporting link from one of the patient pages (for example, the reporting link 419 from the screen of FIG. 6) takes the user to the screen (or pops up the screen) of FIG. 22. While one of ordinary skill in the art will appreciate, based on the present disclosure, the wide array of possible reports that could be generated by the patient data management platform or system 100 based on the data fields shown and described, one particular example is discussed. The report generation dialog box permits a program to be selected for a particular patient (in order to permit different reports to be generated for each program, e.g., community paramedicine program, in which the patient is listed, which permits separate reports to be sent to separate providers or types of providers). The report generation dialog box of FIG. 22 also permits a report type to be selected, and provides a text entry field for the user to describe the purpose of the report which will be generated along with the report and displayed therein as a note to the viewer of the report. For a "program summary" report selection, a report similar to that of FIG. 24 will be generated, for example in portable document format ("PDF") or other electronic format, which may be mailed, e-mailed, faxed, or otherwise sent to another person or location. For a "visit status" report selection from the screen of FIG. 22, the user will also be prompted on the screen of FIG. 22 to select a visit date for which the report is desired, and a report similar to that of FIG. 23 will be generated detailing the particular patient visit.

Figure 23:
Figure 28:
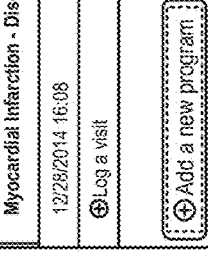

Details and functionality have been described above for logging a visit (see FIG. 3 module 306) with respect to FIGS. 11 through 21, reviewing patient information (see FIG. 3 module 308) with respect to FIGS. 6 through 10, and generating a report (see FIG. 3 module 310) with respect to FIGS. 22 through 24. New patients may be added to the patient data management platform or community paramedicine system (see FIG. 3 modules 302) in various ways. As one example, the user may select the "add a patient" link from the introductory screen shown in FIG. 5, which takes the user to a screen similar to that of FIG. 25, where the user enters information about the patient as shown in the user input fields. FIG. 26 is a bottom portion of the screen of FIG. 25, or may be a different screen associated with new patient addition. After the new patient's bibliographic information and other information called for in FIGS. 25 and 26 is entered, and the "continue" link is selected, the user is taken to the screen of FIG. 27, which permits programs, goals, and program status information to be associated with the patient. For example, as described above, the user may enter the date of referral, the information about who the referral was received by, the referral source (for example the hospital or care facility which referred the patient to the community paramedicine program), and the referrer. The user may also be prompted to associate the patient with one or more program types (e.g., "evaluate and refer," "chronic obstructive pulmonary disease," "congestive heart failure," "hotspotter", and "myocardial infarction"). The screen of FIG. 27 may also prompt for the date of patient contact, the identity of the person contacting the patient, and the manner in which the patient was contacted, as well as the program status and date of first visit. FIG. 28 illustrates a screen with a patient overview for a patient with Myocardial Infraction. FIG. 29 illustrates a screen with a patient overview for a patient that is associated with both an "evaluate and refer" program and a "congestive heart failure" program type, as displayed in the left-hand column. The screen of FIG. 27 may further prompt the user for information about one or more program goals, for example stopping system abuse, keeping the patient out of the hospital for a number of days (e.g., following discharge), evaluating and triaging the patient for a potential emergency room visit, and other goals. When a patient is added to one or more programs with the screen of FIG. 27, the user may also note whether certain tasks have been completed, for example consent received, regulatory notices provided, and/or discharge instructions provided, as well as add notes in narrative format regarding the patient.

Figure 27:
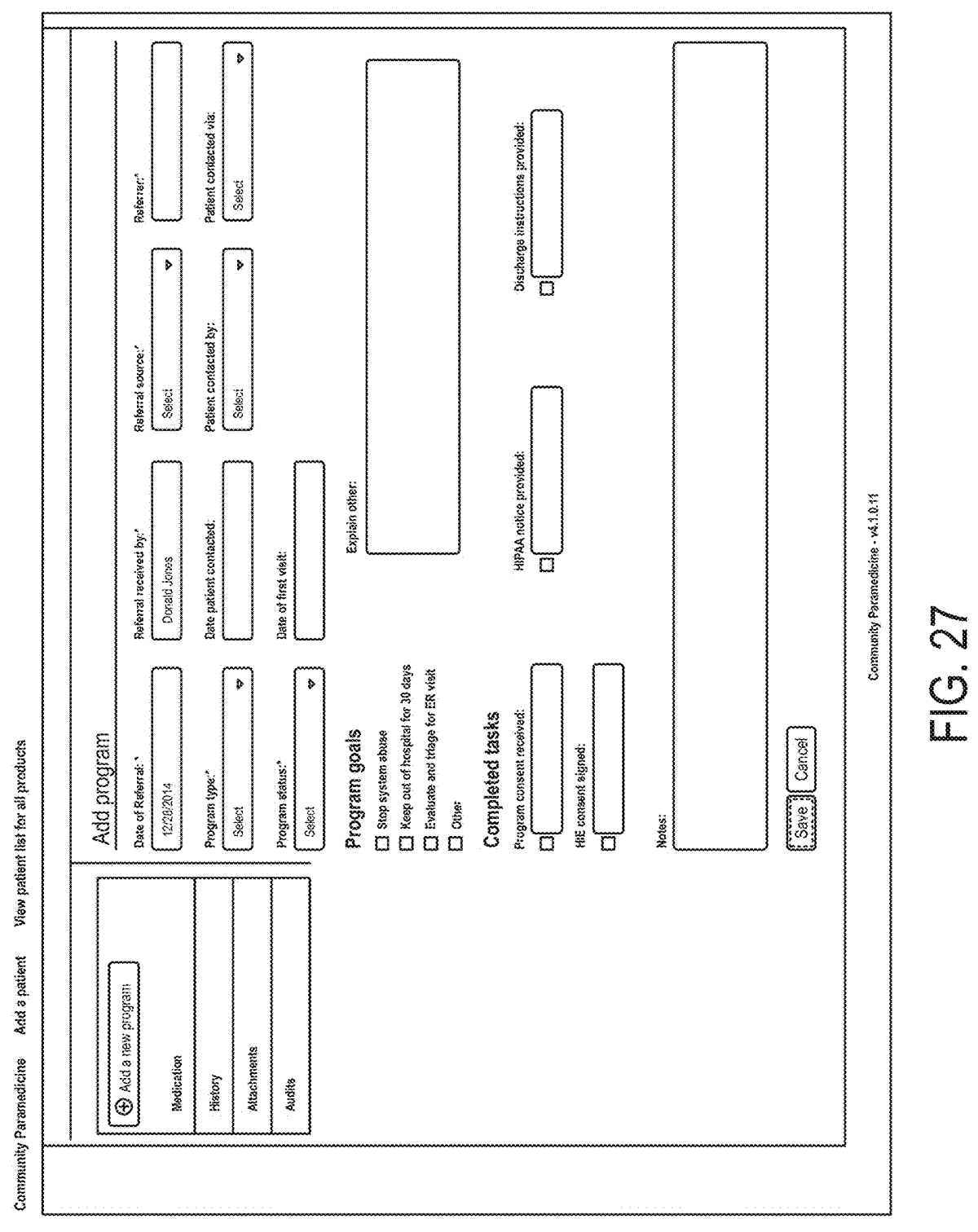

Selecting the "program details" link for a particular patient, for example in the screen view of FIG. 6, takes the user to a screen similar to that of FIG. 27, except fields that were previously populated are displayed in an "edit program" format, permitting the user to adjust or modify some or all of the program information for the patient. Also, selecting the link for an existing patient's name, for example selecting "Ben Franklin" from the screen of FIG. 6, takes the user to a screen similar to that of FIGS. 25 and 26, except fields that were previously populated are displayed in an "edit patient" format, permitting the user to adjust or modify some or all of the patient information.

In addition to adding a new patient with the "add a patient link" from, for example, the screen of FIG. 5, a patient may also be added by selecting an existing patient that is part of another service associated with the same medical information database 130 as the community paramedicine system 100. For example, selecting the "view patient list for all products" link 404 from the screen of FIG. 5 takes the user to a screen similar to FIG. 30. Clicking on the name of a patient from the screen of FIG. 30 links the user to a screen similar to that of FIGS. 25 and 26 to "edit a patient," followed by a screen similar to that of FIG. 27 with which the patient, who existed in the database for purposes of another product offered to the same company, can be associated with the patient data management platform, e.g., a community paramedicine platform and one or more goals or program types or program status selections associated with the community paramedicine platform, according to some embodiments. In all of the aforementioned ways, and more, a new patient may be added to the system (see FIG. 3, module 302) and/or a patient's information or status may be edited (see FIG. 3, module 304).

Finally, the company subscribing to the patient data management platform 100 (and, potentially, other platforms or products offered by the same provider, for example those shown on the screen of FIG. 4) may have an ability to administer certain parameters regarding the patient data management platform 100. For example, when a user who is authorized to administrate the platform 100 enters an administration area, the user may be presented with selections such as those shown on FIG. 31. Each selection may permit the user to customize or import or otherwise select potential data fields, ranges, or data sets to serve as drop-down menus or selectable fields within the platform 100. For example, the administrator can decide on the list of procedures, medications, and medical history descriptions available for input when logging visits by the paramedic to the patient, among other parameters. This may also be the user interface where the administrator user can set parameters for the one or more data verification and/or alerting fields described above, according to some embodiments of the present disclosure. According to some embodiments, an administrator (e.g., the highest-level user(s) of a particular customer of platform 100) can add a "reference library" including documents to which users 114, 124 can refer, with such reference library including, without limitation, an agency's protocols, drug information (e.g., including contraindications), community resources to which patients may be referred by users, and/or the like.

Figure 32:
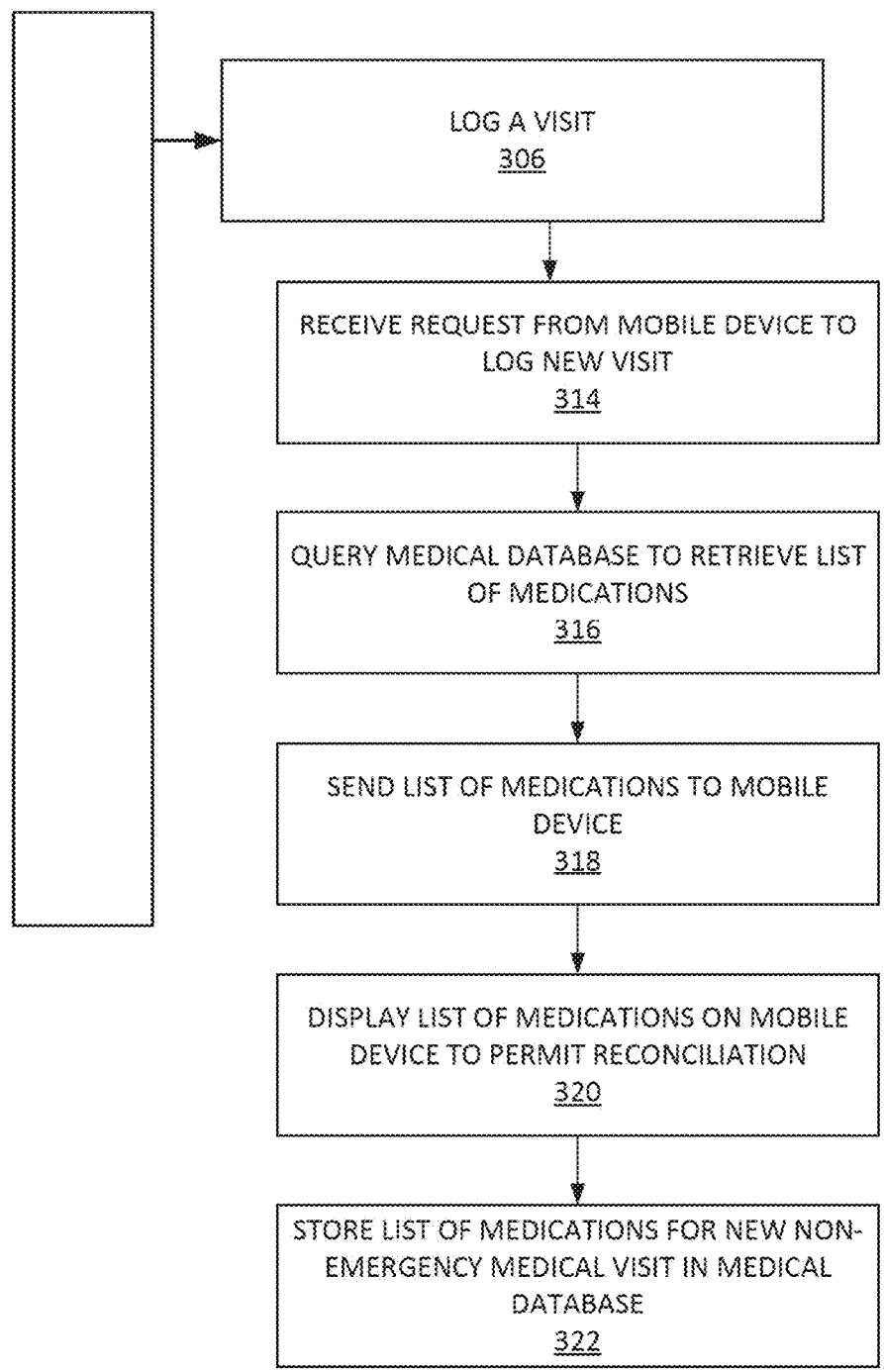
FIG. 32 illustrates a flow chart for a medication reconciliation method accomplished by embodiments of the present disclosure.
Figure 33:
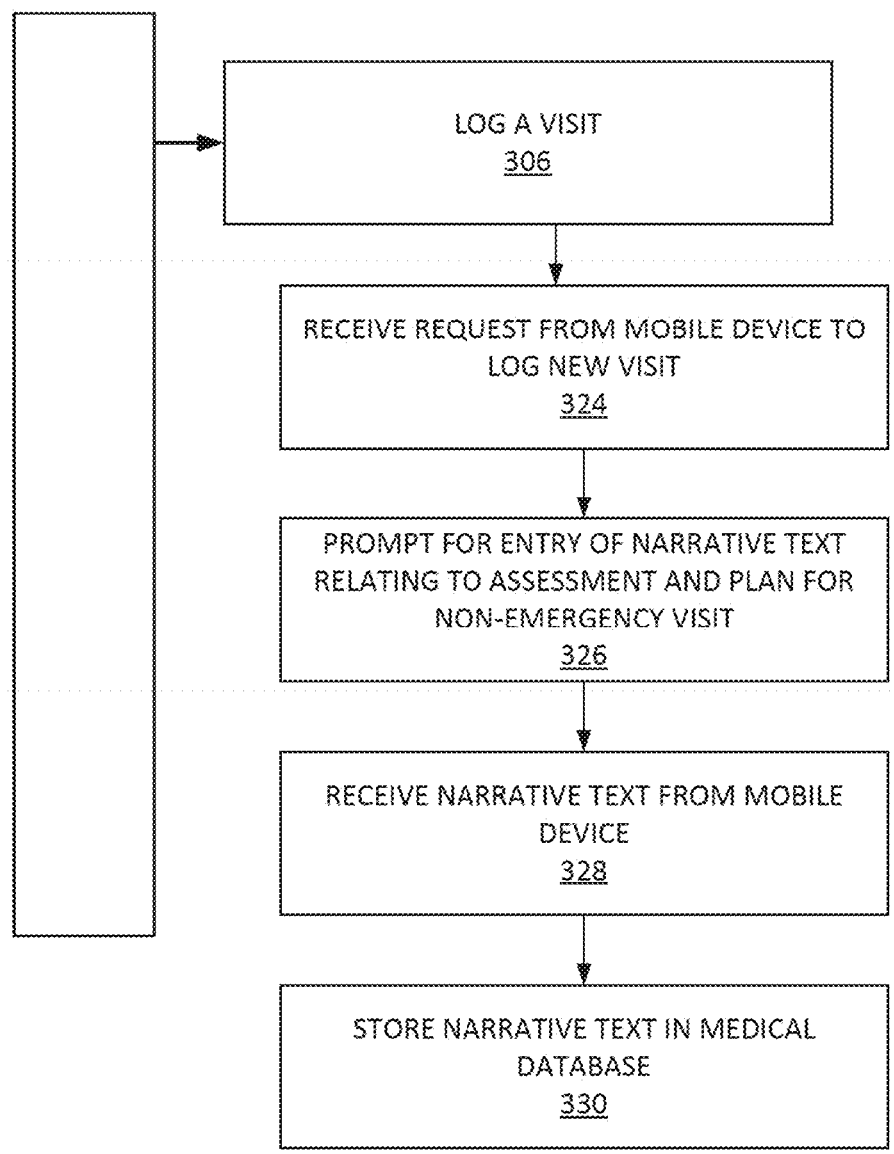
FIG. 33 illustrates a flow chart for a goal, program plan, and assessment narrative entry method accomplished by embodiments of the present disclosure.
Figure 34:
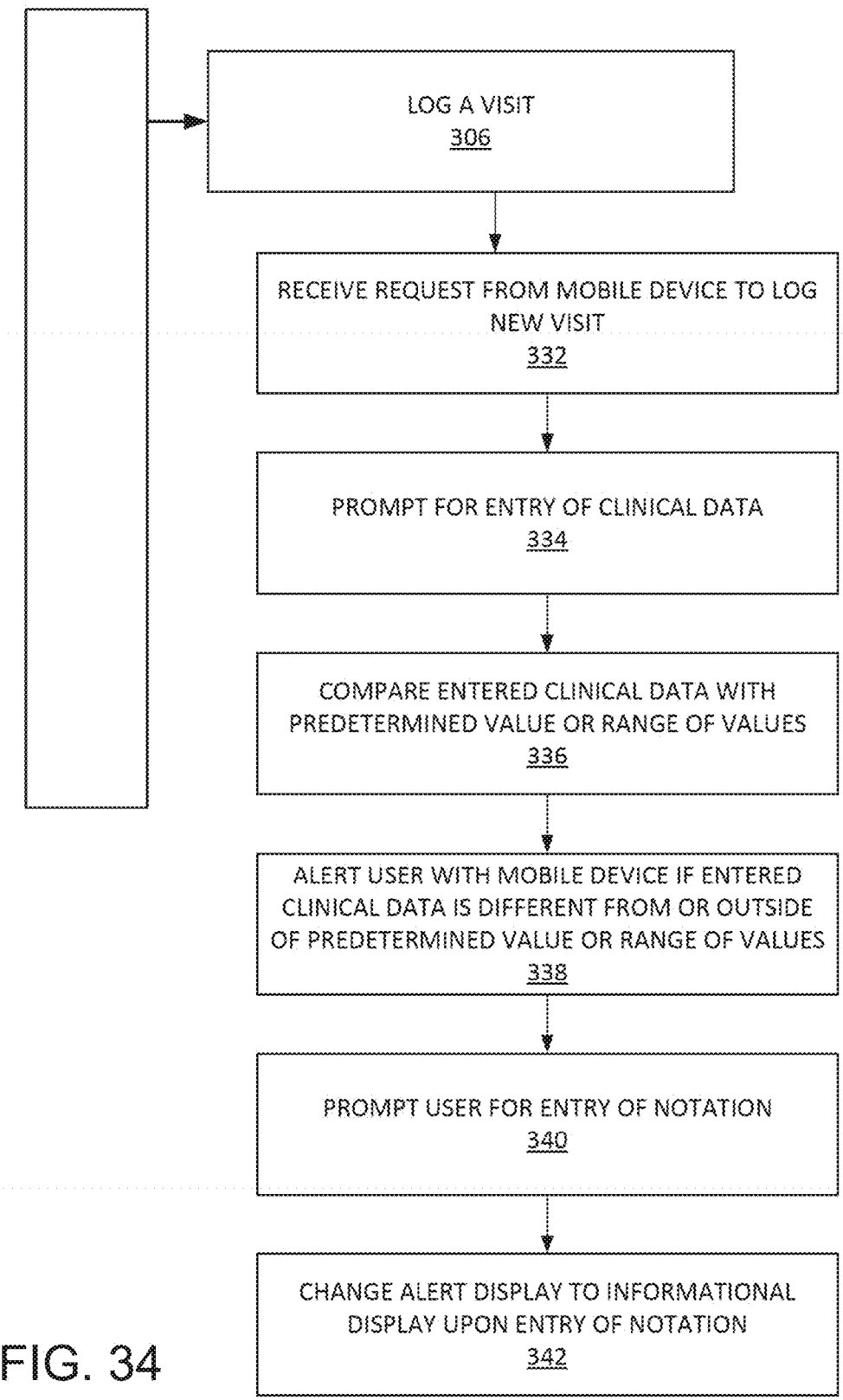
FIG. 34 illustrates a flow chart for a data verification and alerting method accomplished by embodiments of the present disclosure.

FIGS. 32-34 illustrate additional detail about various methods accomplished by embodiments of the present disclosure. FIG. 32 illustrates a flow chart for a medication reconciliation method accomplished by embodiments of the present disclosure. FIG. 33 illustrates a flow chart for a goal, program plan, and assessment narrative entry method accomplished by embodiments of the present disclosure. FIG. 34 illustrates a flow chart for a data verification and alerting method accomplished by embodiments of the present disclosure.

As shown in FIG. 32, when the user selects the links to log a visit (block 306), a request is received from the mobile device 108 to the server 126 and/or 128 to log a new visit (block 314). In some cases, if the mobile device 108 is unable to connect when the request to log a visit is made, the mobile device 114 may log the visit in a local database (e.g., 118) and transmit the visit log data to servers 124 and/or 128 when a connection to network 120 is available. When the user is viewing the patient medication information or entering new medication information (as shown, for example, in FIGS. 7, 13, and 19), the medical database 130 may be queried to retrieve a list of medications associated with the patient (block 316), and the list may be sent to the mobile device 108 (block 318). The mobile device 108 may display the list of medications received from the medical information database 130 in order to permit the user 114 to reconcile the information received during the patient visit with existing information about the patient's medications (block 320). Based on the visual information and/or the reconciliation, the user may enter or revise the list of medications based on the new non-emergency medical visit, and cause them to be stored in the medical database (block 322).

As shown in FIG. 33, when the user selects the links to log a visit (block 306), a request is received from the mobile device 108 to the server 126 and/or 128 to log a new visit (block 324). When the user is entering a new patient, or logging a visit, the user is prompted for entry of narrative text relating to the goals, programs, assessment, and plan for the patient or the non-emergency visit (block 326). Examples of this are discussed, above, with respect to FIGS. 20, 21, and 27. The narrative text may be received from the mobile device 108 (block 328), and stored in the medical database 130 (block 330). Such narrative text regarding a patient's goals, community paramedicine programs or other programs, subjective observations, objective observations, assessment, and plan are typically not collected or tracked during emergency or EMS visits, whose goals are instead to immediately stabilize the patient and transport them if necessary.

As shown in FIG. 34, when the user selects the links to log a visit (block 306), a request is received from the mobile device 108 to the server 126 and/or 128 to log a new visit (block 332). When the user is prompted for the entry of clinical data (block 334), the entered clinical data is compared to a predetermined value or range of values (block 336), and the user is alerted (for example, on the display of the mobile device 108) if the entered clinical data is different from the predetermined value or outside the predetermined range (block 338). The user may be prompted, along with or after or in conjunction with the alert, to enter a notation or observations about the alert or warning (block 340), and upon entry of such a note into the patient data management platform 100, the alert may be changed to an informational display that provides access by the user to the notation (block 342). Examples of this functionality are discussed, above, with respect to FIGS. 14 through 17, according to embodiments of the present disclosure.

Figure 35:
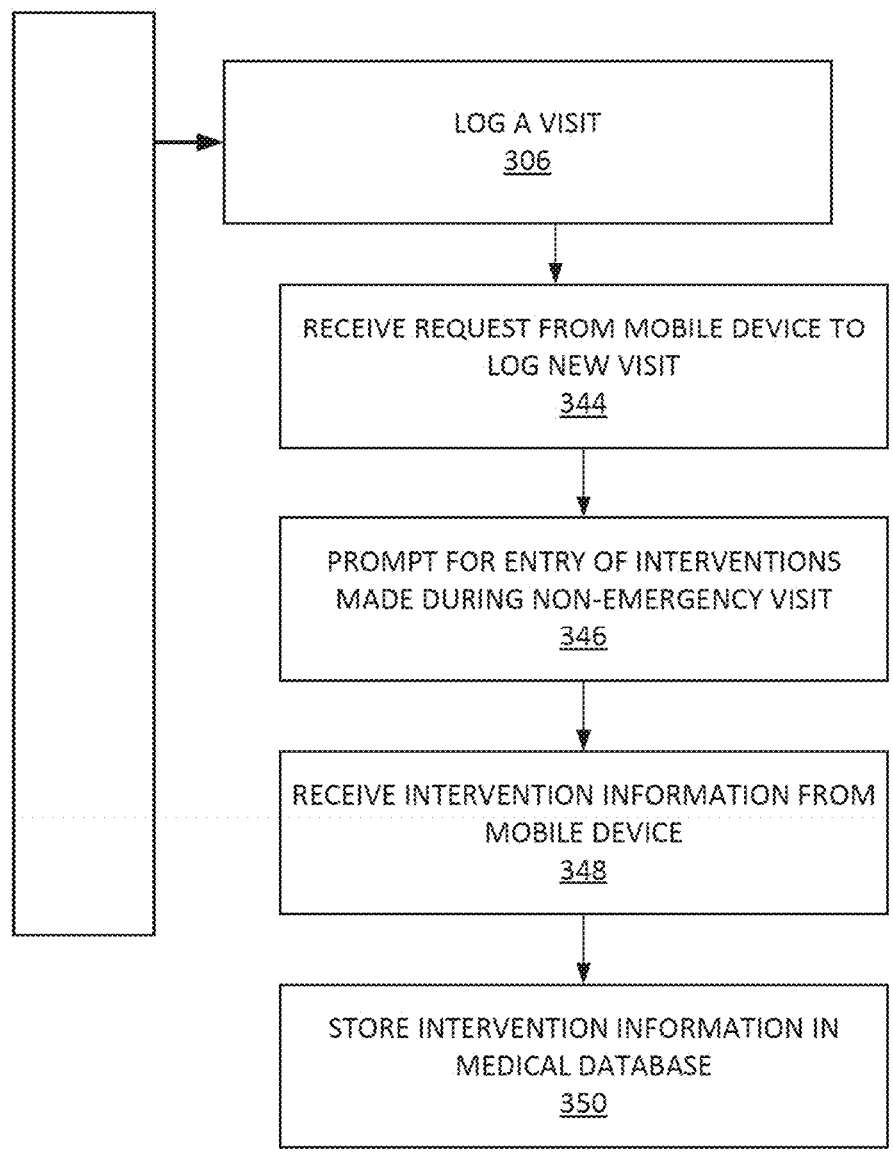
FIG. 35 illustrates a flow chart for a patient intervention entry method accomplished by embodiments of the present disclosure.

As shown in FIG. 35, when the user selects the links to log a visit (block 306), a request is received from the mobile device 108 to the server 126 and/or 128 to log a new visit (block 344). The user is prompted for the entry of data relating to interventions made by the user during the visit, e.g., a non-emergency medical visit (block 346), and such intervention information is received by the server 126 and/or 128 from mobile device 108 (block 348) and stored in a medical information database (e.g., 130) (block 350). Such prior intervention information may also be retrieved by the mobile device 108 from servers 126 and/or 128 and displayed during patient visit logging and/or as part of a user's 114 review of the patient's 116 medical history or prior or current status within the patient data management platform 100, according to embodiments of the present disclosure. Display and/or entry of such intervention information is shown and described above with respect to FIGS. 6, 19, 21, and 24, according to embodiments of the present disclosure.

As discussed above, the mobile computing device 108 may be communicably coupled to other devices such as medical devices that provide some or all of the values associated with data fields shown or described herein. For example, medical device 106 may be defibrillator coupled to the patient 116. Other such devices which may be communicably coupled to the mobile computing device 108 and/or the community paramedicine platform either sequentially and/or simultaneously include, but are not limited to, a blood analyzer (e.g., an i-STAT handheld blood analyzer), a pulse oximetry monitor, a blood pressure monitor, a heart rate monitor, a blood glucose monitor, an optical hematocrit monitor, a blood pH monitor, a respiration rate monitor, an intravenous pump system, a thermometer, a scale, a ZOLL Autopulse® device, a ZOLL LifeVest® device, an automatic external defibrillator, a heart sound monitor, a lung sound monitor, a navigation system, a patient charting system, a vehicle/driver safety system, a computer-aided dispatch system, a patient scheduling system, a health information exchange (HIE) system, patient temperature management system, a spirometer, a ventilator, an imaging system (including, for example, an imaging result analysis system), an ultrasound system, and/or a radiological system. Embodiments of a patient data management platform 100 may also communicably couple with personal health monitors and/or personal mobile smart devices, for example personal activity monitors (e.g., Fitbit systems), smart watches, smart phones, personal heads-up display computers (e.g., Google Glass), and other personal devices. In some cases, such devices are coupled to network 120 and/or server 126 and/or 128 and provide data values for the patient which are stored in database 130 and/or sent to mobile computing device 108 for entry into the patient data management system 100.

According to some embodiments of the present disclosure, the enterprise user 124 is a referrer or a referral source, and the enterprise workstation 122 is used to access a portal into the patient data management platform 100 via network 120, whereby the referrer 124 can refer a patient to the patient data management platform 100 and/or to a community paramedicine program. Such a user 124 may have its login information authenticated in a manner that allows the user to add patients to the patient data management platform 100 as described above; such a user 124 may alternatively have a lower level of security credentials which allow the user to alert or trigger an alert to another higher-level user of the patient data management platform 100 to inquire about or initiate the entry of a new patient to the platform 100.

According to some embodiments of the present disclosure, the enterprise user 124 is a physician 124 who uses the physician's workstation 122 to view information about the physician's patients (e.g., in a format similar to those shown and described with respect to FIGS. 4 to 31), and/or track their patients' progress over time, within, e.g., a community paramedicine system. Such physician's access credentials may permit the physician to view only those patients associated with the physician and/or referred by the physician or the physician's practice, according to some embodiments.

According to some embodiments, the enterprise user 124 is a patient who accesses a patient portal into the patient data management platform 100 using patient workstation 122. Using such portal, the patient 124 can view the patient's information and/or track their progress in the program, for example in a format similar to that shown in FIGS. 4 to 31. Other portal access may be created for other enterprise users 124, which permits the enterprise user 124 to see and/or edit all or a subset of data in the patient data management platform 100. User 124 access may be set up by an administrator 134 or another enterprise user 124 as a role-based access so that a particular user sees information according to their role or level within the patient data management platform 100; for example, one physician 124 may be able to view all of the information relating to that physician's patients within the patient data management platform or community paramedicine system, while that physician 124 may be equipped with no access to view the patients of other physicians or providers, according to embodiments of the present disclosure.

According to some embodiments, the enterprise user 124 is a customer of the patient data management system 100 who logs in through the customer's workstation 122 and utilizes pre-built dashboards, statistics, and/or reports to evaluate the performance of that customer's community paramedicine program. In some cases, customers may create their own dashboards using all or some subset of the data fields available in the patient data management system 100. Such performance statistics may be configured to be devoid of patient-identifying information, and/or otherwise HIPAA compliant. The patient data management system 100 may be further configured to allow each customer to compare their implementation of a community paramedicine system or other system with the implementations of other customers in a manner that assists in evaluating performance of the system and/or of the personnel associated with the system, for example in a manner that does not reveal patient-specific data from other customers.

According to some embodiments of the present disclosure, the patient data management system 100 may be configured to generate reports based on the data in its databases 130 for use by researchers, lawmakers, and other interested public and nonpublic constituencies to assist them in improving patient outcomes, adjusting spending strategies, and the like. Such reports may include a graph, plot, or text output of any and/or all and/or additional data fields similar to those described and shown with respect to FIGS. 4 to 31.

In some embodiments of the present disclosure, the one or more databases (e.g., 130, 118, and others) include instructions that, when executed by the device 108 and/or 126 and/or 128, cause the mobile device 108 to direct the user 114 in the care being provided based on protocols or treatment pathways. Such protocols or treatment pathways may be set up or specified by an administrator at the agency that is a customer of the patient data management platform 100, for example, and/or may be or include protocols set forth by the government or regulatory agencies, or industry-wide or standard protocols. Such protocols may include reminders to capture certain vital signs, asking the patient certain questions, educating the patient on certain procedures that may be performed by or on themselves, and the like. For example, such protocols or treatment pathways may include clinical decision support ("CDS"), which may be used by hospitals or physician clinics to meet regulatory criteria (e.g., "Meaningful Use Criteria"). As such, CDS systems may provide decision support or assistance to the clinician 114 by providing the correct information (e.g., knowledge, reports, suggestions, warnings, and the like), to the correct people (e.g., the care provider or the patient or other user), through the appropriate channels (e.g., devices, technology, software), in the correct interventional format (e.g., checklists, order sets, dashboards, reports, treatment protocols), at the correct point (e.g., in time) in the workflow (e.g., intervention) for decision making an action.

According to some embodiments of the present disclosure, the disclosed systems and methods can help decrease hospital readmission rates, help patients achieve patient-specific goals, and help reduce emergency room visits. The following examples illustrate scenarios in which a mobile integrated health platform, such as platform 100, may be used to assist with setting, tracking, monitoring, and/or evaluating patient treatment plans and/or treatment goals.

Example 1—Congestive Heart Failure

The following example of a patient suffering from Congestive Heart Failure (CHF) can demonstrate how the disclosed systems and methods implemented in a community paramedicine (CP) or mobile integrative health (MIH) program, can decrease hospital readmission rates. CHF is one of several conditions identified by Medicare with a very high rate of hospital readmission within 30 days of hospital discharge. Through a partnership with a hospital, emergency medical services can have an ongoing community paramedicine program to provide home visits to CHF patients during the 30-days post-admission period. This program can use defined protocols to assess, monitor, and adjust each CHF patient's care during the 30-days post-admission period.

For example, described using the flow chart of FIG. 3, after a patient is released from the hospital after a one-week admission for CHF, the patient may be added as a new patient to the CP/MIH platform (block 302—FIG. 3). This may be accomplished, for example, by using the "Add a patient" feature illustrated in the screen shot of FIG. 5, as well as inputting the information fields shown in FIGS. 25-27. For example, for this particular CHF patient, in the "Add program" interface of FIG. 27, the "Program type" may be selected as "congestive heart failure," and the "program status" may be selected as "discharged." The patient's information may be updated (block 304—FIG. 3) to indicate the dates of his CHF treatment, and/or to set a goal for the patient (e.g. avoid readmission for CHF for 30 days). A date may be entered for the discharge, and the box may be selected under "Program goals" (in the screen shot of FIG. 27) corresponding to "Keep out of hospital for 30 days." One or more visits may be scheduled and logged (block 306—FIG. 3), for example the first visit may be set to occur within 24 hours of the patient's discharge from the hospital.

Upon scheduling of the visit, the disclosed platform can generate documentation that the health care provider can use during the visit. For example, during the initial visit, the patient can be enrolled in the CP/MIH program using the platform and interface on a computing mobile device carried by the health care provider, such as the interface shown in FIGS. 5 and 25. In addition, using the platform on the computing mobile device, the health care provider can enter information about the patient's medical history (FIG. 8), vital signs (FIGS. 14-17), current medications (FIGS. 7 and 13), and overall health status. For example, the health care provider can use a user interface like the one shown in FIGS. 6-24 to enter such evaluation and/or treatment information. As used in the present disclosure, evaluation and/or treatment information may include clinical or nonclinical information. As used in the present disclosure, evaluation information may be, for example, information about a patient's vital signs measured during the visit or other information generated during or obtained by an evaluation of the patient. As used in the present disclosure, treatment information may be, for example, information about medications administered to a patient during the visit or other information generated about treatment of or interactions with the patient.

During this initial visit, and/or when the patient is set up in the CP/MIH platform, program goals may be defined for the patient, which in a case of a CHF patient can include preventing a hospital readmission for a minimum of 30 days. To achieve this goal, the health care provider or another user set up a program plan for the patient. First, the health care provider can make sure the patient has filled in the platform and obtained his prescribed medication. The plan can also specify, for example, that the patient's weight does not increase more than five pounds, and that the patient keeps all of his scheduled outpatient physician appointments. This information may be entered, for example, in the interface of FIG. 27 by also checking the "Other" box under "Program goals," and then putting narrative text in the "Explain other" box to reflect that the goal is that the patient's weight does not increase more than five pounds (e.g. over a certain time period) and/or that the patient keeps all scheduled outpatient physician appointments (e.g. over a certain time period). Similar information may alternatively or duplicatively be included in the "Notes" narrative box of FIG. 27. The platform can be used to schedule and document ongoing visits by a health care provider, e.g., twice weekly visits, for example using the "Add program" or scheduling features of the platform illustrated in FIG. 27. Based on the disclosure provided herein, one of ordinary skill in the art will recognize that a wide array of various program goals and/or time periods or deadlines may be set as the goal for the patient and/or the platform.

During subsequent health care provider visits, if any part of the program plan is not followed, the platform can alert the health care provider, for example by displaying or sending a report to the health care provider (block 310—FIG. 3). This report may be in the form of the report of FIG. 24, for example as a status report for the primary care physician. The platform 100 may be configured to deliver or push such a report electronically to the user's (e.g. physician's) mobile computing device via web browser interface with the physician. For example, if the patient's weight was increased by 8 pounds (e.g. if the report of FIG. 24 stated under a heading "Vital Signs Summary" that on date Dec. 27, 2014 the patient's weight was 200 pounds and on date Dec. 28, 2014 the patient's weight was 208 pounds, or that the patient experienced an 8 pound weight increase), which can indicate an increased amount of edema and fluid build-up, using a CHF protocol implemented on the computing mobile device, the health care provider can contact the patient's physician and receive an order to administer 80 mg of Lasix IV to the patient and recheck the patient after eight hours. During the follow-up visit, the health care provider can check whether the patient's weight had decreased to an appropriate range, and also check other vital signs, e.g., whether the patient's oxygen saturation levels had improved. During such follow-up visit, the reports of FIGS. 23 and/or 24, and/or other reports indicating any or all information from the addition of the patient, the scheduling of the visit(s), the selection of the program and/or goal, may be accessible by the health care provider at the visit on the mobile computing device of the health care provider. As illustrated in FIGS. 23 and/or 24, such information may be in the form of a compilation of information (of any type) entered into the platform for the patient on any current or prior visit or occasion.

Once the health care provider enters the new patient information in the platform, the platform can provide instructions for additional orders to increase the patient's oral Lasix intake to 80 mg by mouth for the next three days. The health care provider can continue with the remaining scheduled visits to ensure the patient was able to stabilize his CHF at home, and achieve the goal, avoiding the 30 day hospital readmission. In one embodiment, the primary care physician enters the community paramedicine platform after 30 days, and the platform displays a report similar to that of FIG. 24, and the primary care physician sees, based on the compilation of information in the Interventions Summary that the patient has avoided hospital readmission over the last 30 days. Such a report may also include an outright indication of the progress of the patient toward the goal, for example, it could say "Program goal achieved: patient kept out of hospital for 30 days."

In this manner, the CP/MIH platform prompted the health care provider to enter information, such as evaluation and treatment information of the patient associated with the at least one program goal, in two or more subsequent non-emergency visits, such as two or more non-emergency medical visits, during the particular time period. In this particular example, and others throughout the present disclosure, the CP/MIH platform may prompt the health care provider for any information that relates to the CP/MIH platform; for example, the platform may prompt for only evaluation information, only treatment information, or for both evaluation and treatment information, in addition to being able to prompt for other types of information. Examples of evaluation and/or treatment information, and/or the fields that may prompt for such information or such types of information, are illustrated in FIGS. 5-31. The CP/MIH platform enabled the display of an indication of progress of the patient in meeting the program goal, in this case to avoid readmission to the hospital for 30 days after being treated for CHF. This information was accessible to the patient, the health care provider, the EMS company or government provider, and/or the discharging hospital via the CP/MIH platform. For example, the indication is a compilation of information entered during the visits, displayed in a manner so as to qualitatively indicate whether the patient is progressing toward the goal (for example, by including narrative information such as "patient's edema appears to have decreased" or "dermal areas exhibit less puffiness"), and/or displayed in a manner so as to quantitatively indicate whether the patient is progressing toward the goal (for example, "after 15 days the patient has not been readmitted" or "goal met: patient avoided readmission for 30 days").

Example 2—Diabetes

The following example of a patient with diabetes can demonstrate how the disclosed systems and methods can help patients achieve patient-specific goals. This example may also be accomplished using the process of FIG. 3, as well as the various user interface screens and fields, and corresponding report generation or alerting features, as described above. Diabetes is a metabolic disease that impacts the body's ability to produce any or enough insulin. The lack of insulin results in increased blood glucose levels and, over time, several other conditions including a decreased ability to heal wounds and avoid infection. The incidence of diabetes, and its related conditions, is growing within the United States. Through a partnership with a hospital, emergency medical services can have an ongoing community paramedicine program to provide home visits to diabetic patients with non-healing extremity wounds. The program can use defined protocols to assess, monitor, and adjust each patient's care, for example, during a 60-day treatment period.

For example, a diabetic patient can be referred to the community paramedicine program for enrollment and evaluation of a left leg wound that is currently being managed by a diabetic program. The health care provider can schedule a visit using the disclosed platform. The platform can generate relevant documentation for the particular patient and the particular type of program. During the initial visit, e.g., within twenty four hours from the request, the patient can enroll or be enrolled into the CP/MIH program using the disclosed platform. Using an interface on a computing mobile device, the health care provider can collect patient information about the patient's medical history, vital signs, current medications, and overall health status. In addition, during the initial visit, the patient and health care provider can establish goals, which can include for example, the "improvement of wound healing over a 60-day treatment period." To achieve this goal, the health care provider can set a plan that could help the patient.

For example, the health care provider can confirm that the patient has filled and obtained their prescribed medication. The platform can also provide a list of the actions the health care provider can do towards successful completion of the goal. For example, using an interface on the computing mobile device the health care provider can document the patient's blood glucose levels. The computing mobile device can also list treatment or procedures appropriate for the particular patient, e.g., the platform can suggest that the health care provider can change the wound dressings and check whether the wound is healing and not becoming infected. The health care provider can also confirm with the patient that they will keep all of the patient's scheduled outpatient physician appointments. In addition, using the platform, the health care provider can schedule follow up visits, with the appropriate frequency, e.g., daily for the first 2 weeks, then 3 times per week for the remainder of the 60-day period.

If, during one of the subsequent visits, the health care provider notices that the patient's wound has increased drainage with evidence of superficial infection, and/or has increased in size, using a diabetic wound management protocol implemented on the computing mobile device, the health care provider can address the situation. For example, the health care provider can contact the patient's physician, can transmit a photo of the wound, and can receive an order to administer the appropriate drug and dosage, e.g., 2 g of Vancomycin IV to the patient. During the following visit, the health care provider can check whether the patient's wound has improved. Based on the condition of the wound, the heath care provider can receive orders to administer the appropriate drug to the patient, e.g., daily for a total of one week. Over the remainder of the 60-days, the health care provider can check, via the CP/MIH platform, whether the condition of the wound has improved, achieving the overall program goal.

Example 3—Mental Health/Substance Abuse

According to some embodiments of the present disclosure, the disclosed systems and methods can help communities manage more effectively and cost-efficiently connecting mental health/substance abuse patients with the correct types of resources. This example may also be accomplished using the process of FIG. 3, as well as the various user interface screens and fields, and corresponding report generation or alerting features, as described above. Mental health issues, often presenting as substance abuse, can be common to most communities resulting in an EMS dispatch and patient evaluation. These patients challenge the traditional EMS system, as their need must be triaged to the appropriate medical, public safety, or mental health resource. Since these cases are often complex, any non-medical disposition by EMS typically requires a medical evaluation in the emergency department first. Instead of burdening emergency departments with initial examinations, EMS community paramedicine services can provide this initial evaluation and successfully assist each mental health/substance abuse patient in receiving the correct resource.

For example, when the police are called to assist with a mental health issue, they often contact EMS as they are uncomfortable taking away the patient without medical clearance. EMS community paramedicine can be dispatched to perform an initial screening. On arrival at the scene, the health care provider can use the platform to register the patient in a mental health and/or substance abuse program. The program can have a goal for example, to place the patient into the mental health system without consuming expensive emergency department resources or placing the patient at undue risk. The patient's history can be obtained from previous EMS events. The health care provider can confirm, after vital signs have been checked, and after a physical and a psychological exam, whether the patient is at his baseline and in no danger to himself or to others. The health care provider can contact a medical director by radio and review the mental health/substance abuse protocol. The health care provider can contact the community's mental health center to discuss the patient. If the mental health center accepts the patient, the patient can be transported to the mental health center by law enforcement. The mental health center can accept the EMS community paramedicine evaluation as medical clearance, avoiding a costly, resource-consuming emergency department visit. The details of this encounter can be documented using an interface on a computing mobile device as described herein, and the health care provider or other user can confirm that the goal has been achieved.

According to some embodiments of the present disclosure, the program goal for a mental health/substance abuse patient can be to reduce the patient's use of EMS services over a particular time period, for example to reduce the number of emergency room transports/visits by 80% over a two-month period. Such a program goal may be time based. According to other embodiments of the present disclosure, the program goal for a mental health/substance abuse patient can be to evaluate and triage the patient for potential emergency room transport/visit; according to such embodiments, the predetermined number of visits may be one, with the goal being to evaluate and/or triage the patient during that one visit based on prior visits to determine whether the patient needs to be transported to the emergency room for that particular visit, or whether instead a transport or referral to a mental health facility or program would be possible.

Example 4—High Frequency EMS Users

Every community has what are often referred to as EMS "loyal customers". These are individuals who do not have an emergency but frequently call 911 requesting EMS services to assist them. They often present with a complaint such as "chest pain" to qualify for transport to the emergency department. Once they arrive at the emergency department, their true need is quickly verbalized: in some cases, these individuals were seeking a warm place to sleep, a meal, or simply transportation (e.g. to a location closer to home). Most EMS systems define a "loyal customer" as anyone who contacts EMS more than once per month for 2 or more consecutive months. EMS Community Paramedicine is often used to address "loyal customers" as they have a significant impact on the overall EMS resources available for true emergencies within a community.

When a high-frequency EMS user calls 911 requesting EMS services for chest pain, the 911 center can identify him or her as a "loyal customers," e.g., from a list of documented high-frequency EMS users, and can dispatch the EMS community paramedicine program. This example may also be accomplished using the process of FIG. 3, as well as the various user interface screens and fields, and corresponding report generation or alerting features, as described above. On arrival, the health care provider can interview the patient and note the frequency of calls to 911 requesting EMS services. During the interview, the health care provider can identify patterns, e.g., each time the patient states he has chest pain, is transported to the same emergency department, and quickly leaves after he has received a meal. The information received during the interview and measured vital signs can all be documented using the disclosed platform, e.g., through an interface running on a computing mobile device. The patient can be enrolled in a high-frequency EMS user community paramedicine program with a goal of decreasing the patient's EMS use by greater than 50%, or reducing the patient's EMS user by a certain amount over a certain period of time.

The EMS community paramedic can visit the patient at his home for a follow-up visit. During this visit, the patient's interview and examination are entered into the platform. During the home visit, if it is noted that the patient has no food in his home, the health care provider can contact the community's social service resources to provide assistance the patient. The health care provider can schedule visits to the patient weekly. During these visits, several other community resources are identified to assist the patient. The CP/MIH platform may include data entry fields (e.g. the "Social History" field of FIG. 8, or the "Narrative" fields of FIGS. 20 and 21) in which the healthcare provider can note non-emergency needs of the patient in order to refer the patient to other community resources. Over the next 3 months, the health care provider can schedule less frequent visits to help identify community resources for the patient, for example community resources that would help reduce the patient's need to call 911, and help subsequently achieve the goal.

Various modifications and additions can be made to the exemplary embodiments discussed without departing from the scope of the present disclosure. For example, while the embodiments described above refer to particular features, the scope of this invention also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A patient data management system for community paramedicine, the system comprising:
a medical database configured to store, for a patient, a patient record comprising a patient-specific program goal for the patient to reduce his/her use of emergency medical services (EMS) by a quantified amount during or within a particular time period or within a predetermined number of encounters with a healthcare provider;
at least one mobile computing device configured to provide a portal screen to a patient data management platform;
at least one medical device configured to communicatively couple to the at least one mobile computing device and configured to:
couple to the patient;
measure patient data comprising vital signs for the patient; and
provide the patient data comprising the vital signs to the at least one mobile computing device; and
a server hosting the patient data management platform and configured to be in communication with the at least one mobile computing device, the server comprising a processor and a memory, the memory including instructions executable to:
provide instructions at the portal screen to prompt a user to enter information about the patient associated with the patient-specific program goal and obtained during a first encounter with the patient;
cause the at least one mobile computing device to automatically record patient data received from the at least one medical device during the first encounter with the patient;
provide instructions at the portal screen to prompt the user to enter information about the patient associated with the patient-specific program goal and obtained during one or more second encounters with the patient outside a health care facility, the information about the patient obtained during the one or more second encounters comprising information about travel of one or more emergency medical service professionals to a patient location;
cause the at least one mobile computing device to automatically record patient data received from the at least one medical device during the one or more second encounters with the patient;
receive, via the portal screen, the user entered information about the patient obtained during the first encounter and the one or more second encounters;

determine that at least some of the user entered information about the patient is outside a predetermined range;

in response to the determination, display, on the portal screen, (a) a warning with an alert icon indicating that the at least some of the user entered information about the patient is outside the predetermined range and (b) a data entry field;

receive and store a user entry to the data entry field comprising information regarding the at least some of the user entered information about the patient that is outside the predetermined range;

in response to receiving and storing the user entry to the data entry field, replace the alert icon with a selectable information icon that enables the user to view the user entry to the data entry field upon selection of the information icon; and use (a) at least some of the user entered information about the patient obtained during the first encounter and the one or more second encounters, and (b) at least some of the automatically recorded patient data received during the first encounter and the one or more second encounters to verify whether the patient reduced his/her use of the EMS by the quantified amount;

wherein the patient-specific program goal is specific to a high frequency EMS user;

wherein the server is communicatively coupled to an emergency dispatch service and is configured to receive an identification of the patient as the high frequency EMS user; and wherein the memory further includes instructions executable to prompt the user of the portal screen to collect information that identifies a pattern of emergency calls by the patient.

2. The patient data management system of claim 1, the memory further including instructions executable to:

compare (a) at least some of the user entered information obtained during the one or more second encounters and at least some of the automatically recorded patient data received during the one or more second encounters to (b) at least some of the user entered information obtained during the first encounter and at least some of the automatically recorded patient data received during the first encounter; and alert the user regarding an inconsistency between (a) the at least some of the user entered information obtained during the first encounter, (b) the at least some of the user entered information obtained during the one or more second encounters, and (c) the at least some of the automatically recorded patient data received during the one or more second encounters.

3. The patient data management system of claim 1, wherein the particular time period spans at least thirty days.

4. The patient data management system of claim 1, wherein the medical database is further configured to store, for the patient, an additional patient-specific program goal that is specific to one or more of a congestive heart failure, wound healing, substance abuse, and mental health.

5. The patient data management system of claim 1, wherein the predetermined number of encounters is one, and the user entered information obtained during the first encounter, the user entered information obtained during the one or more second encounters, the automatically recorded patient data received during the first encounter, and the automatically recorded patient data received during the one or more second encounters collectively includes notation of non-emergency needs of the patient to refer the patient to other community resources.

6. The patient data management system of claim 1, wherein the first encounter and the one or more second encounters comprise emergency medical services visits to the patient location, wherein the user is the healthcare provider, wherein the first encounter and the one or more second encounters are encounters between the healthcare provider and the patient, wherein the at least one mobile computing device is configured to be carried with the healthcare provider during at least one of the one or more second encounters between the healthcare provider and the patient, and wherein the user entered information obtained during the first encounter and the user entered information obtained during the one or more second encounters collectively comprises evaluation and/or treatment information.

7. The patient data management system of claim 1, the patient-specific program goal further for achieving no readmission of the patient to a hospital.

8. The patient data management system of claim 1, wherein the server is communicatively coupled to a medical billing system and is configured to extract billing information for one or more of the patient and a neighborhood.

9. The patient data management system of claim 8, wherein the billing information is associated with one or more of Medicare, Medicaid, and commercial insurance payments.

10. A patient data management system for community paramedicine, the system comprising:

a medical database configured to store a plurality of patient records, each patient record comprising a patient-specific program goal for a patient comprising meeting a condition during or within a time period or within a predetermined number of visits;

at least one mobile computing device configured to provide a portal screen to a patient data management platform, the at least one mobile computing device comprising a tablet or smartphone;

a server hosting the patient data management platform and configured to be in communication with the medical database and the at least one mobile computing device, the server comprising a processor and a memory, the memory including instructions executable to:

provide instructions at the portal screen to prompt a user to enter information about the patient associated with the patient-specific program goal and obtained during a first encounter with the patient and one or more second encounters with the patient, receive, via the portal screen, the user entered information about the patient obtained during the first encounter and the one or more second encounters;

determine that at least some of the user entered information about the patient is outside a predetermined range;

in response to the determination, display, on the portal screen, (a) a warning indicating that the at least some of the user entered information about the patient is outside the predetermined range, (b) an alert icon with the warning, and (c) a data entry field;

receive and store a user entry to the data entry field comprising information regarding the at least some of the user entered information about the patient that is outside the predetermined range;

in response to receiving and storing the user entry to the data entry field, replace the alert icon with a selectable information icon that enables the user to view the user entry to the data entry field upon selection of the information icon;

use at least some of the user entered information about the patient obtained during the first encounter and the one or more second encounters to provide an indication of progress of the patient in achieving the patient-specific program goal; and prompt the user of the portal screen to collect information that identifies a pattern of emergency calls by the patient;

wherein the patient-specific program goal is specific to a high frequency emergency medical services (EMS) user; and wherein the server is communicatively coupled to an emergency dispatch service and is configured to receive an identification of the patient as the high frequency EMS user.

11. The patient data management system of claim 10, wherein at least one of the first encounter and the one or more second encounters comprises an encounter with at least one emergency medical service professional located somewhere other than a patient location.

12. The patient data management system of claim 10, wherein the server is configured for cloud-based operation in which the server implements the patient data management platform for a plurality of mobile computing devices including the at least one mobile computing device.

13. The patient data management system of claim 10, wherein the server is communicatively coupled to at least one workstation at a location remote from a location of the at least one mobile computing device.

14. The patient data management system of claim 10, wherein the memory comprises instructions executable to provide data entry fields at the portal screen for one or more of a visit log, medications, vitals, lab results, interventions, and caregiver narrative.

15. The patient data management system of claim 10, wherein the memory comprises instructions executable to provide a social history data entry field at the portal screen configured to receive non-emergency medical needs of the patient.

16. The patient data management system of claim 10, comprising at least one medical device configured to communicatively couple to at least one of the server and the at least one mobile computing device and configured to:

couple to the patient;

measure patient data comprising vital signs for the patient; and provide the patient data comprising the vital signs to the at least one of the server and the at least one mobile computing device;

wherein the memory comprises instructions executable to cause the at least one mobile computing device to automatically record patient data received from the at least one medical device.

17. The patient data management system of claim 16, wherein the memory comprises instructions executable to use at least some of the automatically recorded patient data to provide the indication of progress of the patient in achieving the patient-specific program goal.

18. The patient data management system of claim 17, wherein the at least one medical device is a portable defibrillator.

19. The patient data management system of claim 10, wherein the memory comprises instructions executable to:

query the medical database to retrieve a list of medication for the patient; and send the list of medication to the at least one mobile computing device.

20. The patient data management system of claim 19, wherein the memory comprises instructions executable to:

display the list of medication at the portal screen;

receive user revisions of the list of medication to generate a reconciled list of medication; and store the reconciled list of medication in the medical database.

21. The patient data management system of claim 10, wherein the memory comprises instructions executable to provide clinical decision support to the user via the portal screen.

22. The patient data management system of claim 10, wherein the memory comprises instructions executable to measure performance of a community relative to a community goal, the community comprising a set of patients associated with a same patient-specific program goal, the set of patients corresponding to a set of patient records from the plurality of patient records.

23. The patient data management system of claim 22, wherein the community goal comprises reducing a frequency of use of EMS by the community for a particular time period.

24. The patient data management system of claim 10, wherein the server is communicatively coupled to a medical billing system and is configured to extract billing information for one or more of the patient and a neighborhood.

25. The patient data management system of claim 24, wherein the billing information is associated with one or more of Medicare, Medicaid, and commercial insurance payments.

* * * * *